United States Patent
Pike et al.

(10) Patent No.: US 10,815,230 B2
(45) Date of Patent: Oct. 27, 2020

(54) CASEIN KINASE 1 DELTA INHIBITOR

(71) Applicant: ELECTROPHORETICS LIMITED, London (GB)

(72) Inventors: Ian H. Pike, Cobham (GB); Karsten Kuhn, Hofheim am Taunus (DE); Stefan Kienle, Frankfurt am Main (DE); William D. O. Hamilton, Orwell (GB); Jonathan R. Heal, Nottingham (GB); Joseph M. Sheridan, Royston (GB)

(73) Assignee: ELECTROPHORETICS LIMITED, London (GB)

( * ) Notice: Subject to any disclaimer, the term of this patent is extended or adjusted under 35 U.S.C. 154(b) by 0 days.

(21) Appl. No.: 15/574,099

(22) PCT Filed: May 13, 2016

(86) PCT No.: PCT/EP2016/060918
§ 371 (c)(1),
(2) Date: Nov. 14, 2017

(87) PCT Pub. No.: WO2016/180981
PCT Pub. Date: Nov. 17, 2016

(65) Prior Publication Data
US 2018/0186786 A1    Jul. 5, 2018

(30) Foreign Application Priority Data

May 14, 2015 (GB) .................................. 1508276.1
Sep. 29, 2015 (GB) .................................. 1517197.8

(51) Int. Cl.
| | | |
|---|---|---|
| *C07D 471/04* | (2006.01) | |
| *A61P 25/28* | (2006.01) | |
| *A61P 25/16* | (2006.01) | |
| *A61K 31/437* | (2006.01) | |

(52) U.S. Cl.
CPC .......... *C07D 471/04* (2013.01); *A61K 31/437* (2013.01); *A61P 25/16* (2018.01); *A61P 25/28* (2018.01)

(58) Field of Classification Search
CPC combination set(s) only.
See application file for complete search history.

(56) References Cited

FOREIGN PATENT DOCUMENTS

WO    WO 2012/080727 A2    6/2012

OTHER PUBLICATIONS

FDA (Aricept, 2012). (Year: 2012).*
Chauhan, A. et al.; "Amyloid β-protein stimulates casein kinase I and casein kinase II activities"; Brain Research, vol. 629, 1993, pp. 47-52.
Corcoran, N.M. et al.; "Sodium selenate specifically PP2A phosphatase, dephosphorylates tau and reverses memory deficits in an Alzheimer's disease model"; Journal of Clinical Neuroscience, vol. 17, 2010, pp. 1025-1033.
Ghoshal, N. et al.; "A New Molecular Link between the Fibrillar and Granulovacuolar Lesions of Alzheimer's Disease"; American Journal of Pathology, vol. 155, No. 4, Oct. 1999, pp. 1163-1172.
Gonzalez, I. et al.; "Selective Monomethylation of Anillnes by Cu(OAc)2-Promoted Cross-Coupling with MeB(OH)2"; Organic Letters, vol. 11, No. 8, 2009, pp. 1677-1680.
Hanger, D.P. et al.; "Novel Phosphorylation Sites in Tau from Alzheimer Brain Support a Role for Casein Kinase 1 in Disease Pathogenesis"; The Journal of Biological Chemistry, vol. 282, No. 32, Aug. 10, 2007, pp. 23645-23654.
International Search Report issued for PCT/EP2016/060918, dated Jun. 29, 2016.
Karaman, M. et al; "A quantitative analysis of kinase inhibitor selectivity"; Nature Biotechnology, vol. 26, No. 1, Jan. 2008, pp. 127-132.
Lanzilliotta, A. et al.; "The γ-Secretase Modulator CHF5074 Reduces the Accumulation of Native Hyperphosphorylated Tau in a Transgenic Mouse Model of Alzheimer's Disease"; Journal of Molecular Neuroscience, vol. 45, 2011, pp. 22-31.
Lemercier G. et al.; "Identification and Characterization of Novel Small Molecules as Potent Inhibitors of the Plasmodial Calcium-Dependent Protein Kinase 1"; Biochemistry, vol. 48, No. 27, 2009, pp. 6379-6389.
Lipinski, C.A. et al.; "Experimental and computational approaches to estimate solubility and permeability in drug discovery and development settings"; Advanced Drug Delivery Reviews, vol. 46, 2001, pp. 3-26.
Long, A. et al.; "Structural Basis for the Interaction between Casein Kinase 1 Delta and a Potent Selective Inhibitor"; Journal of Medicinal Chemistry; vol. 55; 2012; pp. 956-960.
O'Brien, P. et al.; "High Content Screening: A Powerful Approach to Systems Cell Biology and Drug Discovery"; Methods in Molecular Biology Edited by Taylor et al.; pp. 415-425.

(Continued)

*Primary Examiner* — Umamaheswari Ramachandran
(74) *Attorney, Agent, or Firm* — Arent Fox LLP

(57) ABSTRACT

The present invention provides 2-Methyl-amino-3-[(4-fluorophenyl)carbonyl]indolizine-1-carboxamide of formula (I) or a pharmaceutically acceptable salt thereof;

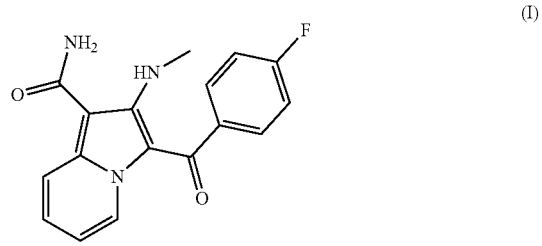

and its therapeutic uses in the treatment of neurodegenerative disorders, in particular tauopathies and most preferably in the treatment of Alzheimer's disease.

17 Claims, 4 Drawing Sheets

(56) References Cited

OTHER PUBLICATIONS

Peters, J.M. et al.; "Casein kinase I transduces Wnt signals"; Nature, vol. 401, Sep. 23, 1999, pp. 345-350.
Verkaar, F. et al.; "Inhibition of Wnt/β-Catenin Signaling by p38 MAP Kinase Inhibitors Is Explained by Cross-Reactivity with Casein Kinase 1δ/ε"; Chemistry & Biology, vol. 18, Apr. 22, 2011, pp. 485-494.
Wager, T.T. et al.; "Moving beyond Rules: The Development of a Central Nervous System Multiparameter Optimization (CNS MPO) Approach To Enable Alignment of Druglike Properties"; ACS Chemical Neuroscience, vol. 1, 2010, pp. 435-449.
Wang, J. et al.; "Grape Derived Polyphenols Attenuate Tau Neuropathology in a Mouse Model of Alzheimer's Disease"; Journal of Alzheimers' Disease, vol. 22, 2010, pp. 653-661.
Yasojima, K. et al.; "Casein kinase 1 delta mRNA is upregulated in Alzheimer disease brain"; Brain Research, vol. 865, 2000, pp. 116-120.

\* cited by examiner

CASEIN KINASE 1 DELTA INHIBITOR

CROSS-REFERENCE TO RELATED APPLICATIONS

This application is the U.S. National Stage Application of International Patent Application No. PCT/EP2016/060918 filed on May 13, 2016, which claims priority to GB Application No. 1508276.1.4, filed on May 14, 2015, and GB Application No. 1517197.8, filed on Sep. 29, 2015 the contents of each of which is incorporated herein by reference in its entirety.

FIELD OF THE INVENTION

The present invention relates to 2-Methyl-amino-3-[(4-fluorophenyl)carbonyl]indolizine-1-carboxamide, an inhibitor of casein kinase 1 delta, pharmaceutically acceptable salts and pharmaceutical compositions thereof in the treatment of neurodegenerative disorders such as Alzheimer's disease.

BACKGROUND OF THE INVENTION

Casein kinase 1 belongs to the serine/threonine kinase family. In mammals, it is known in seven isoforms, namely, alpha, beta, gamma 1 to 3, delta and epsilon. A potential role of mammalian casein kinase 1 delta in neurodegenerative disorders, such as Alzheimer's disease (AD), has been hypothesized. Casein kinase 1 delta is increased more than 30-fold in the hippocampus of patients with AD compared to control subjects (Ghoshal, N. et al. (1999) Am J Pathol 155, 1163-1172), while its mRNA is increased 24-fold (Yasojima, K et al. (2000) Brain Res 865, 116-120). Amyloid beta-peptide (Aβ), a component of the senile neuritic plaque that together with tangles (of which PHF tau is the main component), characterises AD, appears to stimulate casein kinase 1 activity (Chauhan, A et al. (1993) Brain Res 629, 47-52). In addition, it has been confirmed that 5 newly identified Serine/Threonine phosphorylation sites in PHF tau (insoluble tau, also called paired helical filament tau, an extremely phosphorylated aggregate obtained from the lesions in the brains of AD's patients) can be generated by casein kinase 1 delta, bringing the total number of phosphorylation sites on adult tau to 10, three of which are exclusively phosphorylated by casein kinase 1 delta (Hanger D P et al. (2007) J Biol Chem 282, 23645-23654).

These findings support that casein kinase 1 delta may make an important contribution to the pathogenesis of AD and other neurodegenerative diseases. In fact, intraneuronal deposit of tau in the form of typical neurofibrillary tangles is not an exclusive feature of AD.

Morphologically distinct tau aggregates, all filamentous and mostly in a hyperphosphorylated state, are found in other neurodegenerative disorders such as frontotemporal dementia with Parkinsonism linked to chromosome 17 (FTDP-17), progressive supranuclar palsy (PSP), Pick's disease, corticobasal degeneration, ad multisystem atrophy (MSA) which are all grouped as teuopathies. This strongly implies that similar abnormalities in regulating phosphorylation of taxi are shared by all the teuopathies.

Casein kinase 1 delta inhibitors therefore may be of potential benefit in the treatment of AD and other neurodegenerative disorders, such as tauopathies. WO2012080727 discloses casein kinase 1 delta inhibitors which show inhibition of greater than 90% in a casein kinase 1 delta assay and also show some degree of selectivity against other kinases.

Hence, there remains the need for a casein kinase inhibitor with therapeutic benefit in the treatment of neurodegenerative disorders such as AD and other tauopaties which retains inhibition against casein kinase 1 delta whilst it shows improved casein kinase 1 delta selectivity and brain permeability.

SUMMARY OF THE INVENTION

The present invention, therefore, provides in a first aspect 2-Methyl-amino-3-[(4-fluorophenyl)carbonyl]indolizine-1-carboxamide, of the structure

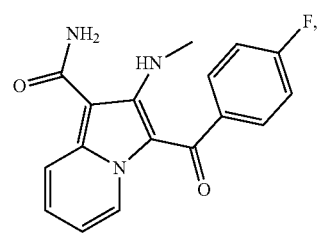 [SMILES: CNc1c(C(N)=O)c2ccccn2c1C(=O)c1ccc(F)cc1]

or a pharmaceutically acceptable salt thereof.

In a second aspect, the invention provides a pharmaceutical composition comprising 2-Methyl-amino-3-[(4-fluorophenyl)carbonyl]indolizine-1-carboxamide of the structure

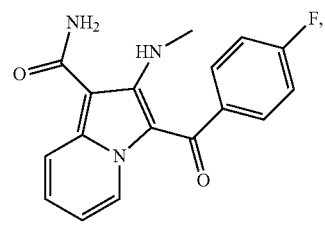 [SMILES: CNc1c(C(N)=O)c2ccccn2c1C(=O)c1ccc(F)cc1]

or a pharmaceutically acceptable salt thereof, and one or more pharmaceutically acceptable carriers or excipients.

In a third aspect, the present invention provides for a combination comprising 2-Methyl-amino-3-[(4-fluorophenyl)carbonyl]indolizine-1-carboxamide of the structure

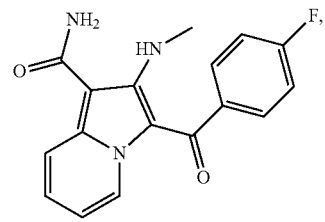 [SMILES: CNc1c(C(N)=O)c2ccccn2c1C(=O)c1ccc(F)cc1]

or a pharmaceutically acceptable salt thereof, and one or more therapeutically active agents.

In a fourth aspect the present invention provides for a method of inhibiting casein kinase 1 delta activity in a subject in need thereof, wherein the method comprises administering to the subject a therapeutically effective amount of 2-Methyl-amino-3-[(4-fluorophenyl)carbonyl]indolizine-1-carboxamide of the structure

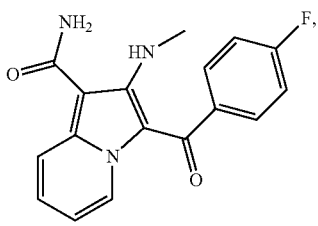

or a pharmaceutically acceptable salt thereof or a pharmaceutical composition thereof.

In a fifth aspect, the present invention provides for a 2-Methyl-amino-3-[(4-fluorophenyl)carbonyl]indolizine-1-carboxamide, of the structure

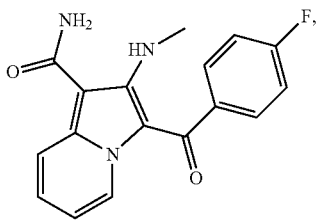

or a pharmaceutically acceptable salt thereof, or a pharmaceutical composition thereof for use as a medicament or in the treatment of a neurodegenerative disorder.

In a sixth aspect the present invention provides for a method of treating a neurodegenerative disorder comprising administering to a subject in need thereof a therapeutically effective amount of 2-Methyl-amino-3-[(4-fluorophenyl)carbonyl]indolizine-1-carboxamide of the structure

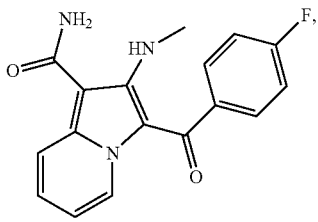

or a pharmaceutically acceptable salt thereof, or the pharmaceutical composition thereof.

Preferably, the neurodegenerative disorder in the fifth and sixth aspect of the invention is a tauopathy such as Alzheimer's disease, frontotemporal dementia with Parkinsonism linked to chromosome 17 (FTDP-17), progressive supranuclear palsy (PSP), Pick's disease, corticobasal degeneration, multisystem atrophy (MSA), neurobasal degeneration with iron accumulation, type 1 (Hallervorden-Spatz), argyrophilic grain dementia, Down's syndrome, diffuse neurofibrillary tangles with calcification, dementia pugilistica, Gerstmann-Straussler-Scheinker disease, myotonic dystrophy, Niemann-Pick disease type C, progressive subcortical gliosis, prion protein cerebral amyloid angiopathy, tangle only dementia, postencephalitic parkinsonism, subacute sclerosing panencephalitis, Creutzfeldt-Jakob disease, amyotrophic lateral sclerosis/parkinsonisia-damentia complex, non-Guamanian motor neuron disease with neurofibrillary tangles/dementia, chronic traumatic encephalopathy, alpha-synucleinopathies and Parkinson's disease.

In one preferred embodiment, the tauopathy is Alzheimer's disease.

DEFINITIONS

Figure 1:
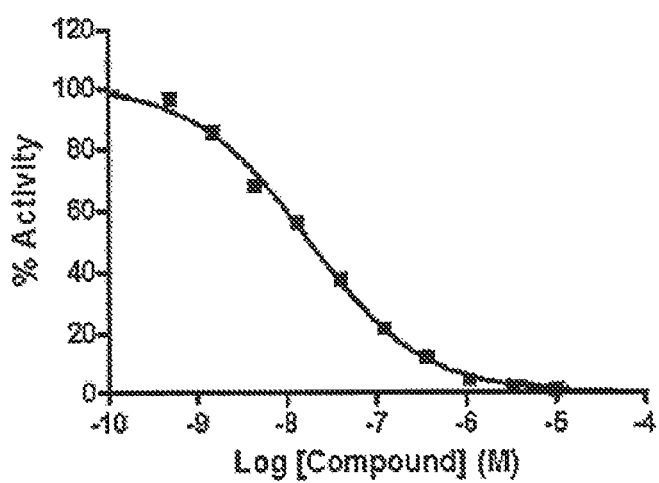
FIG. 1. Casein Kinase 1 delta $IC_{50}$ curve for compound A.

The term "treat", "treating", "treatment", "prevent", "preventing" or "prevention", or grammatical equivalents thereof, includes therapeutic treatments, prophylactic treatments and applications in which one reduces the risk that a subject will develop a disorder or other risk factor. Treatment does not require the complete curing of a disorder and encompasses the reduction of the symptoms or underlying risk factors.

The term "diagnosis", or grammatical equivalents thereof, as used herein, includes the provision of any information concerning the existence or presence, non-existence or absence or probability of the disorder in a patient. It further includes the provision of information concerning the type or classification of the disorder or of symptoms which are or may be experienced in connection with it. This may include, for example, diagnosis of the severity of the disorder, it encompasses prognosis of the medical course of the disorder, for example its duration, severity and the course of progression from mild cognitive impairment (MCI) to AD or other dementias.

As used herein, the term "subject" includes any human or non-human animal. The term "non-human animal" includes all vertebrates, e.g., mammals and non-mammals, such as non-human primates, rodents, sheep, dogs, cats, horses, cows, chickens, amphibians, reptiles, etc.

The term "comprising" indicates that the subject includes all the elements listed, but may, optionally, also include additional, unnamed elements (i.e. open).

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless the context dictates otherwise, the definitions of the features/terms set out above are not limited to any particular aspect or embodiment of the invention and apply equally to all aspects and embodiments which are described herein.

DETAILED DESCRIPTION

One common problem with kinase inhibitors in general is that many of them inhibit multiple kinases, in part because they target the highly conserved ATP-binding pocket. Cross-reactivity, hence, remains one of the main issues when developing kinase inhibitors.

Recent cross-screening data revealed that several widely used compounds for p38α (for instance SB203580) also inhibit casein kinase 1 delta (Verkaar, W et al. (2011) Biochim Biophys Acta 1697, 243-267). Both p38α and casein kinase 1 delta are well known to be activators of the Wnt/β-catenin signaling pathway (Peters J M, et al. (1999) Nature 401, 345-350). Cross-reactivity for p38a and casein kinase 1 delta cannot be explained by sequence similarity as these kinases are quite distant in the phylogenetic tree. Their pharmacological similarity can only be demonstrated by profiling compounds in biochemical assays.

The compound according to the present invention, 2-Methyl-amino-3-[(4-fluorophenyl)carbonyl]indolizine-1-carboxamide, of the structure

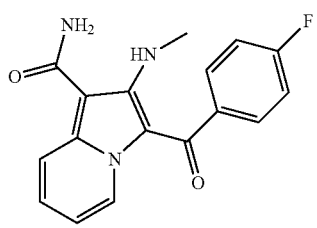 [SMILES: CNc1c(C(N)=O)c2ccccn2c1C(=O)c1ccc(F)cc1]

(which will be also called compound A throughout the description and examples), is derived from compound 987 (2-amino-3-[(4-fluorophenyl) carbonyl]indolizine-1-carboxamide; WO2012080727), whereby the primary amine has been mono-methylated. This development is based on re-modelling the crystal structure of free casein kinase 1 delta, which shows a closed hydrophobic pocket adjacent to the ATP binding site, to an open conformation (model not shown), The model was subsequently confirmed by the recent crystal structure of casein kinase 1 delta in complex with casein kinase 1 delta/epsilon inhibitor PF4800567 (Huang, X et al. (2012) J. Med. Chem. 55: 956-960). The residue defining the ATP binding site (gatekeeper residue) in casein kinase 1 delta is a methionine (Met 85). In contrast the same position in p38α is occupied by a threonine (Thr 106). In our model the primary amine of compound 987 was predicted to form part of the binding interaction with the hinge region of casein kinase 1 delta but also to have the potential to form a hydrogen bond to the side chain of the gatekeeper residue in anti-targets such as to Thr 106 in p38a. The gatekeeper Met 85in casein kinase 1 delta is less adept at forming hydrogen bending via the thioether of its side chain. The mono-methylation of the primary amine reduces interaction with the gate keeper of anti-targets such as p38a but also TGFBR1, ALK4, EGFR, RIPK2, YES, EphA2 and LCK, and also increases potency for casein kinase 1 delta.

In addition, as it will be apparent throughout the examples shown below, compound A not only shows increased selectivity and potency over prior art casein kinase 1 delta inhibitors but also shows good brain permeability and presence in the brain, retains good pharmacological profile and therapeutic benefits, whilst not being cytotoxic, The present invention also provides for the pharmaceutical acceptable salt of 2-Methyl-amino-3-[(4-fluorophenyl) carbonyl]indolizine-1-carboxamide, of the structure

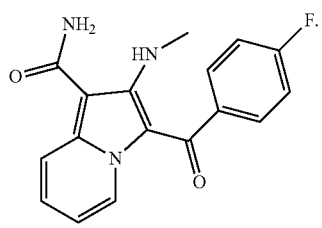 [SMILES: CNc1c(C(N)=O)c2ccccn2c1C(=O)c1ccc(F)cc1]

In the present context, the term "pharmaceutically acceptable salt" is intended to indicate salts which are not harmful to the patient. Such salts include pharmaceutically acceptable acid addition salts, pharmaceutically acceptable metal salts and pharmaceutically acceptable alkaline addition salts. Acid addition salts include salts of inorganic acids as well as organic acids.

Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetraraethylammonium salts and the like.

Representative examples of alkaline salts include, for example, sodium, potassium, lithium, calcium, magnesium or ammonium or organic bases such as, for example, methylamine, ethylamine, propylamine, trimethylamine, diethylamine, triethylamine, N,N-dimethylethanolamine, tris(hydroxymethyl)aminomethane, ethanolamine, pyridine, piperidine, piperasine, picoline, dicyclohexylamine, morpholine, benzylamine, procaine, lysine, arginine, histidine, N-methylglucamine.

According to the invention, 2-Methyl-amino-3-[(4-fluorophenyl)carbonyl]indolizine-1-carboxamide can be in racemic forms, as well as in the form of pure enantiomers or non-racemic (scalemic) mixture of enantiomers.

The present invention also provide for pharmaceutical compositions comprising 2-Methyl- amino-3-[(4-fluorophenyl)carbonyl]indolizine-1-carboxamide, of the structure

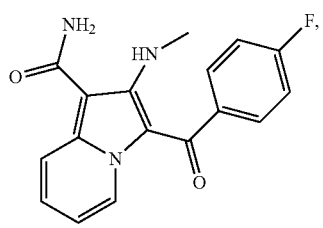 [SMILES: CNc1c(C(N)=O)c2ccccn2c1C(=O)c1ccc(F)cc1]

or a pharmaceutically acceptable salt thereof as described herein and one or more pharmaceutical acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Pharmaceutical compositions for oral administration may be in tablet, capsule, powder or liquid form. A tablet may include a solid carrier such as gelatin or an adjuvant.

Liquid pharmaceutical compositions generally include a liquid carrier such as water, petroleum, animal or vegetable oils, mineral oil or synthetic oil.

Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Combinations of 2-Methyl-amino-3-[(4-fluorophenyl) carbonyl]indolizine-1-carboxamide of the structure

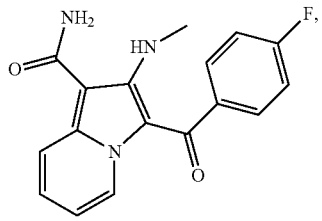

or a pharmaceutically acceptable salt thereof with one or more therapeutically active agents is also encompassed herein.

The one or more therapeutically active agents are preferably agents suitable for the treatment of neurodegenerative disorders, but may also encompass agents suitable for treating side effects of such neurodegenerative disorders such as psychological and mental side effects related to, for example, dementia.

The one or more therapeutically active agents may also encompass anti-amyloid agents, anti-tau antibodies, tau kinase inhibitors, anti-tau aggregation inhibitors.

More preferably, the one or more therapeutically active agents are selected from the group of memantine (e.g. Namenda®), galantamine (e.g. Razadyne®), rivastigmine (e.g. Exelon®), donepezil (e.g. Aricept®), solanezumab, $5HT_s$ antagonists or combinations thereof.

Compound 2-Methyl-amino-3-[(4-fluorophenyl)carbonyl]indolizine-1-carboxamide inhibits casein kinase 1 delta activity and may be used in a method comprising administering to a subject in need thereof compound A or a pharmaceutically acceptable salt thereof or pharmaceutical compositions comprising 2-Methyl-amino-3-[(4-fluorophenyl) carbonyl]indolizine-1-carboxamide or a pharmaceutically acceptable salt thereof or pharmaceutical compositions comprising 2-Methyl-amino-3-[(4-fluorophenyl)carbonyl]indolizine-1-carboxamide or a pharmaceutically acceptable salt thereof.

In one embodiment of the method of inhibiting casein kinase 1 delta activity, the $IC_{50}$ of 2-Methyl-amino-3-[(4-fluorophenyl)carbonyl]indolizine-1-carboxamide is calculated in vitro to be at least 30 nM, more preferably between 20 nM and 30 nM, even more preferably, the in vitro $IC_{50}$ of compound 2-Methyl-amino-3-[(4-fluorophenyl)carbonyl] indolizine-1-carboxamide for use in a method for inhibiting casein kinase 1 delta in a subject in need thereof is less than 20 nM.

The present invention also encompasses 2-Methyl-amino-3-[(4-fluorophenyl)carbonyl]indolizine-1-carboxamide, of the structure

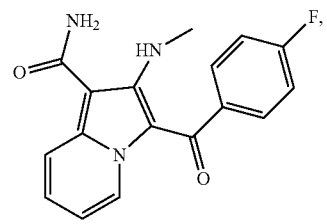 [SMILES: CNc1c(C(N)=O)c2ccccn2c1C(=O)c1ccc(F)cc1]

or a pharmaceutically acceptable salt thereof, or a pharmaceutical composition thereof for use as a medicament or in the treatment of a neurodegenerative disorder or a method of treating a neurodegenerative disorder comprising administering to a subject in need thereof a therapeutically effective amount of 2-Methyl-amino-3-[(4-fluorophenyl)carbonyl]indolizine-1-carboxamide of the structure

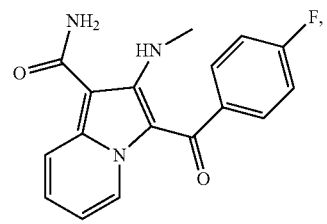 [SMILES: CNc1c(C(N)=O)c2ccccn2c1C(=O)c1ccc(F)cc1]

or a pharmaceutically acceptable salt thereof, or the pharmaceutical composition thereof.

Preferably, the neurodegenerative disorder is a tauopathy. Tauopathies are a recognised class of conditions characterised by neurofibrillary tangles or aggregates of the tau protein. The intracellular deposit of tau protein are usually neuronal or glial, are filamentous and generally they present themselves in a hyperphosphorylated state as compared to the level of phosphorylation in tau from control human brain.

Within the context of the present invention, examples of preferred tauopathies are Alzheimer's disease, frontotemporal dementia with Parkinsonism linked to chromosomes 17 (FTDP-17), progressive supranuclear palsy (PSP), Pick's disease, corticobasal degeneration, multisystem atrophy (MSA), neurobasal degeneration with iron accumulation, type 1 (Hallervorden-Spatz), argyrophilic grain dementia, Down's syndrome, diffuse neurofibrillary tangles with calcification, dementia pugilistica, Gerstmann-Straussler-Scheinker disease, myotonic dystrophy, Niemann-Pick disease type C, progressive subcortical gliosis, prion protein cerebral amyloid angiopathy, tangle only dementia, postencephalitic parkinsonism, subacute sclerosing panencephalitis, Creutzfeldt-Jakob disease, amyotrophic lateral sclerosis/parkinsonism-dementia complex, non-Guamanian motor neuron disease with neurofibrillary tangles/dementia, chronic traumatic encephalopathy, alpha-synucleinopathies and Parkinson's disease.

In one preferred embodiment, the tauopathy is Alzheimer's disease and the present invention encompasses 2-Methyl-amino-3-[(4-fluorophenyl)carbonyl]indolizine-1-carboxamide, of the structure

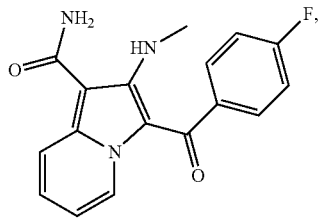

or a pharmaceutically acceptable salt thereof, or a pharmaceutical composition thereof is for use in the treatment of Alzheimer's disease or a method of treating Alzheimer's disease comprising administering to a subject in need thereof a therapeutically effective amount of 2-Methyl-amino-3-[(4-fluorophenyl)carbonyl]indolizine-1-carboxamide of the structure

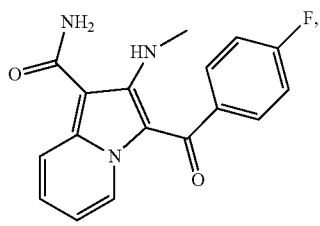

or a pharmaceutically acceptable salt thereof, or the pharmaceutical composition thereof.

Certain aspects and embodiments of the invention will now be illustrated by way of example and with reference to the figures and tables described herein. All documents mentioned in this specification are incorporated herein by reference in their entirety for all purposes.

5. EXAMPLES

Compounds

Compound A (2-methyl-amino-3-[(4-fluorophenyl)carbonyl]indolizine-1-carboxamide) was synthesized in-house according to the synthesis shown herein. Comparative Compound 324 (5-(1,3-benzoxazol-2-yl)-4-(pyridine-4-yl)pyrimidin-2-amine) and Comparative Compound 987 (2-amino-3-[(4-fluorophenyl)carbonyl]indolizine-1-carboxamide) were sourced from Peakdale Molecular®, Comparative Compound 315 (4-((4-methoxyphenyl)methylene)-2-(2-thienyl)-5(4H)-oxalone) and PF4800567 (3-[(3-Chlorophenoxy)methyl]-1-(tetrahydro-2H-pyran-4-yl)-1H-pyrazolo[3,4-d]pyrimidin-4-amine) were sourced from Tocris®.

Abbreviations g gram(s)
h hour(s)
HPLC high performance liquid chromatography
Me methyl
min minute(s)
mg milligram
mL milliliter(s)
mmol millimole
MS mass spectrometry
NMR nuclear magnetic resonance
RT retention time
TOF time of flight
UPLC ultra high performance liquid chromatography

General Conditions

MS analyses were performed on a Q-TOF-2 hybrid quadrupole time of flight mass spectrometer with electrospray ionisation (ESI), coupled with a UPLG (Waters) by direct injection of the sample.

HPLC analyses were performed with an Alliance 2695 HPLC system (Waters) and a Nucleosil 100-5 C18 column from Macherey-Nagel with a 4.6 mm i.d. and a length of 250 mm. Gradient from 100% water to 100% acetonitrile in 42 min, both with 0.1% trifluoroacetic acid.

NMR spectra were run on a Broker AVANCE 500 MHz NMR spectrometer using ICON-NMR, under ToSpin program control. Spectra were measured at 298.2K and were referenced relative to the solvent resonance.

Synthesis of 2-Methyl-amino-3-[((4-fluorophenyl)carbonyl]indolizine-1-carboxamide (Compound A)

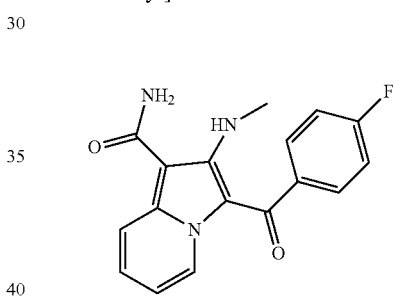

Step 1: Synthesis of 2-chloro-1-(4-fluorophenyl)-pyridinium bromide

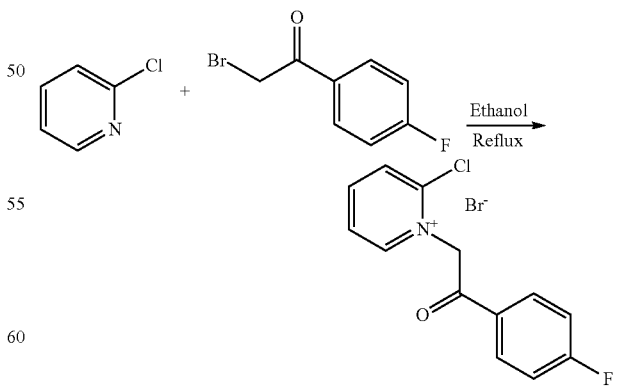

To a solution of 2-bromo-1-(4-fluorophenyl)-ethanone (25 g, 115 mmol) in ethanol (120 ml) was added 2-chloropyridine (32.7 g, 288 mmol) and the reaction was heated to reflux for 5 hours. The solution was left over-night at 4° C.

and the precipitate was filtrated, washed with diethyl ether and dried in vacuo, to yield the title product.

HPLC RT: 17.41 min

LCMS: [M+1]+=250

$^{1}$H-NMR (500 MHz, MeOH-d$_{4}$, δ in ppm: 9.15 (1H, dd, J=6.2 Hz, 1.6 Hz, Pyr-6), 8.75 (1H, ddd, J=8.2 Hz, 8.2 Hz, 1.7 Hz, Pyr-4), 8.44 (1H, dd, J=8.4 Hz, 1.2 Hz, Pyr-3), 8.25 (2H, m, J=9.0 Hz, 5.2 Hz, Ar-2.6), 8.20 (1H, ddd, J=8.4 Hz, 6.3 Hz, 1.4 Hz, Pyr-5), 7.38 (2H, m, J=8.8 Hz, 8.6 Hz, Ar-3.5), 6.67 (2H, s, CH$_{2}$)

Step 2

Synthesis of 2-amino-3-(4-fluorobenzoyl)-indolizine-1-carboxylic acid amide (Pauls H, et al., Chem. Ber, 110, 1294-1303 (1977))

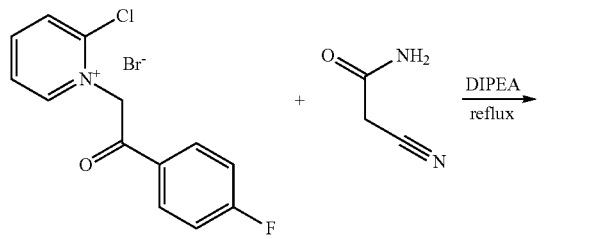

2-Chloro-1-(4-fluorophenacyl)-pyridinium bromide (12.43 g, 37.6 mmol), cyanoacetamide (4.74 g, 56.4 mmol) and N,N-diisopropylethylamine (39.3 ml, 225.6 mmol) in 1-propanol (150 ml) was heated to reflux for 3 hours. The still hot solution was diluted by adding dropwise 90 ml water and was left over-night at 4° C. The precipitate was filtrated, washed with water/1-propanol (1:1) and dried in vacuo to yield the title product.

HPLC RT: 22.65 min

LCMS: [M+1]+=298

$^{1}$H-NMR (500 MHz, DMSO-d$_{6}$), δ in ppm: 9.29 (1H, m, J=6.8 Hz, Ind-4), 7.81 (1H, m, J=8.9 Hz, Ind-7), 7.63 (2H, m, J=8.7 Hz, 5.6 Hz, Ar-2.6), 7.38 (1H, ddd, J=8.9 Hz, 6.9 Hz, 1.1 Hz, Ind-6), 7.30 (2H, m, J=8.9 Hz, 8.8 Hz, Ar-3.5), 7.09 (2H, br s, NH$_{2}$), 6.87 (1H, ddd, J=6.9 Hz, 6.9 Hz, 1.1 Hz, Ind-5), 6.00 (2H, br s, NH$_{2}$)

Step 3: Synthesis of 2-(N-methylamino)-3-(4-fluorobenzoyl)-indolizine-1-carboxylic acid amide (Gonzalez T. et al., Organic letters 11, No. 8, 1677-1680 (2009))

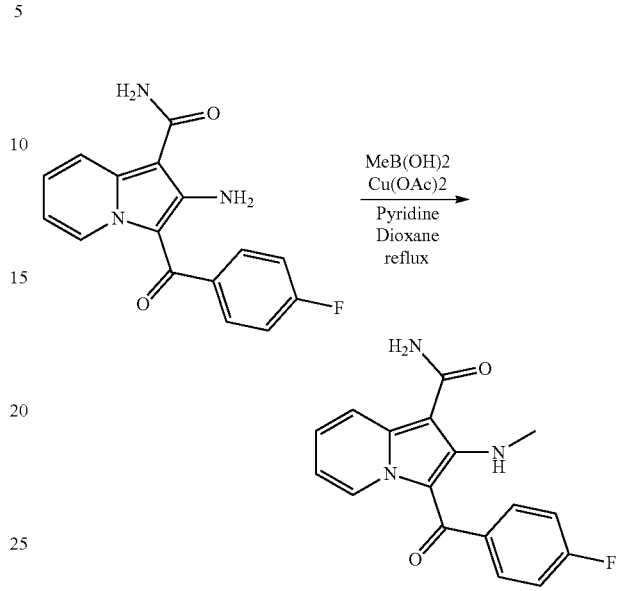

To a solution of 2-amino-3-(4-fluorobenzoyl)-indolizino-1-carboxylic acid amide (3.09 g, 10.4 mmol) and pyridine (2.94 ml, 36.4 mmol) in dioxane (150 ml) was added copper (II) acetate (4.72 g, 26.0 mmol). The solution was stirred for 15 minutes at room temperature, methylboronic acid (2.19 g, 26 mmol) was added and the reaction was heated to reflux for 7 hours. The solution was brought to room temperature, filtrated by means of filter aid and evaporated in vacuo. The residue was dissolved in dichloromethane (400 ml), washed with half-saturated sodium bicarbonate solution (two×230 ml portions), and evaporated to dryness. The residue was purified by column chromatography on neutral aluminum oxide. The reaction may be repeated with recovered educt to enhance the yield.

HPLC rt: 24.14 min

LCMS: [M+1]+=312

$^{1}$H-NMR (500 MHz, DMSO-d$_{6}$), δ in ppm: 9.26 (1H, m, J=7.0 Hz, Ind-4), 7.80 (1H, m, J=8.9 Hz, Ind-7), 7.67 (2H, m, J=8.8 Hz, 5.6 Hz, Ar-2.6), 7.34 (1H, ddd, J=9.0 Hz, 6.9 Hz, 1.1 Hz, Ind-6), 7.30 (2H, m, J=8.8 Hz, 8.8 Hz, Ar-3.5), 7.23 (2H, br s, NH$_{2}$), 7.18 (1H, q, J=5.5 Hz, NH), 6.87 (1H, ddd, J=6.9 Hz, 1.2 Hz, Ind-5), 2.24 (3H, d, J=5.5 Hz, CH$_{2}$)

Biological Data 5.1 Kinase Screening Assay and Binding Capacity

The assay was carried out according to the established KINOMEscan® technology (DiscoveRx® LeadHunter®, Discovery services, www.discoverx.com). This utilises an active site-directed competition binding assay to quantitatively measure interactions between a compound and a kinase. As the assay does not require ATP opposed to the IC$_{50}$ value which may depend on ATP concentration), it reports the true thermodynamic interaction affinity. Compounds that bind the kinase active site and directly (sterically) or indirectly (allosterically) prevent kinase binding to an immobilized ligand, will reduce the amount of kinase captured on a solid support. Conversely, compounds that do not bind the kinase have no effect on the amount of kinase captured on the solid support. Screening "hits" are identified by measuring the amount of kinase captured in test versus control samples by using a quantitative, qPCR method that detects an associated DNA label. For most assays, kinase-tagged T7 phage strains ware grown in parallel in 24-well blocks in an *E. coli* host derived from the BL21 strain. *E. coli* were grown to log-phase and infected with T7 phage from a frozen stock (multiplicity of infection=0.4) and incubated with shading at 32° C. until lysis (90-150 minutes). The lysates were centrifuged (6,000×g) and filtered (0.2 μm) to remove cell debris. The remaining kinases were produced in HEK293 cells and subsequently tagged with DMA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (Sea-Block (Pierce), 1% BSA, 0.05 % Tween 20, 1 mM DTT) to remove unbound ligand and to reduce non-specific phage binding. Binding reactions were assembled by combining kinases, liganded affinity beads, and test compounds in 1× binding buffer (20% SeaBlock, 0.17×PBS, 0.05% Tween 20, 6 mM DTT). Compound A and Comparative Compound 323 were prepared as 40× stocks in 100% DMSO and directly diluted (final concentration 10 μM) into the assay. All reactions were performed in polypropylene 384-well plates in a final volume of 0.04 ml. The assay plates were incubated at room temperature with shaking for 1 hour and the affinity beads were washed with wash buffer (1×PBS, 0.05% Tween 20). The beads were then re-suspended in elution buffer (1×PBS, 0.05 % Tween 20, 0.5 μM non-biotinylated affinity ligand) and incubated at room temperature with shaking for 30 minutes. The kinase concentration in the eluates was measured by qPCR.

Results were reported as "% Ctrl", where lower numbers indicate stronger hits. The calculation of the "% Ctrl" was as follow:

$$\% \; Ctrl = \left[ \frac{Compound \; A \; signal - positive \; control \; signal}{negative \; control \; signal - positive \; control \; signal} \right] \times 100$$

Negative control=DMSO (100% Ctrl)
Positive control=comparative compound 324 (0% Ctrl)

TABLE 1

| Gene Symbol | Cmp 324 % Ctrl @ 10000 nM | Cmp A % Ctrl @ 10000 nM |
|---|---|---|
| AAK1 | 83 | 62 |
| ABL1 (E255K) phosphorylated | 33 | 15 |
| ABL1 (F317I) non-phosphorylated | 90 | 85 |
| ABL1 (F317I) phosphorylated | 100 | 88 |
| ABL1 (F317L) non-phosphorylated | 100 | 88 |
| ABL1 (F317L) phosphorylated | 75 | 46 |
| ABL1 (H396P) non-phosphorylated | 66 | 14 |
| ABL1 (H396P) phosphorylated | 98 | 49 |
| ABL1 (M351T) phosphorylated | 79 | 49 |
| ABL1 (Q252H) non-phosphorylated | 31 | 11 |
| ABL1 (Q252H) phosphorylated | 100 | 37 |
| ABL1 (T315I) non-phosphorylated | 96 | 89 |
| ABL1 (T315I) phosphorylated | 85 | 100 |
| ABL1 (Y253F) phosphorylated | 78 | 50 |
| ABL1 non-phosphorylated | 81 | 42 |
| ABL1 phosphorylated | 98 | 51 |
| ABL2 | 85 | 68 |

TABLE 1-continued

| Gene Symbol | Cmp 324 % Ctrl @ 10000 nM | Cmp A % Ctrl @ 10000 nM |
|---|---|---|
| ACVR1 | 100 | 95 |
| ACVR1B | 100 | 100 |
| ACVR2A | 100 | 98 |
| ACVR2B | 100 | 100 |
| ACVRL1 | 100 | 100 |
| ADCK3 | 88 | 91 |
| ADCK4 | 100 | 84 |
| AKT1 | 96 | 91 |
| AKT2 | 100 | 98 |
| AKT3 | 100 | 100 |
| ALK | 89 | 90 |
| ALK (C1156Y) | 100 | 98 |
| ALK (L1196M) | 100 | 100 |
| AMPK-alpha1 | 98 | 91 |
| AMPK-alpha2 | 100 | 99 |
| ANKK1 | 71 | 68 |
| ARK5 | 100 | 85 |
| ASK1 | 96 | 87 |
| ASK2 | 99 | 100 |
| AURKA | 99 | 91 |
| AURKB | 96 | 86 |
| AURKC | 100 | 100 |
| AXL | 100 | 95 |
| BIKE | 100 | 85 |
| BLK | 80 | 49 |
| BMPR1A | 100 | 100 |
| BMPR1B | 80 | 81 |
| BMPR2 | 100 | 88 |
| BMX | 100 | 91 |
| BRAF | 77 | 93 |
| BRAF (V600E) | 59 | 86 |
| BRK | 99 | 92 |
| BRSK1 | 98 | 100 |
| BRSK2 | 100 | 94 |
| BTK | 92 | 88 |
| BUB1 | 44 | 44 |
| CAMK1 | 100 | 100 |
| CAMK1D | 96 | 97 |
| CAMK1G | 89 | 65 |
| CAMK2A | 99 | 70 |
| CAMK2B | 100 | 62 |
| CAMK2D | 99 | 78 |
| CAMK2G | 100 | 87 |
| CAMK4 | 89 | 96 |
| CAMKK1 | 100 | 89 |
| CAMKK2 | 97 | 82 |
| CASK | 78 | 77 |
| CDC2L1 | 91 | 85 |
| CDC2L2 | 100 | 91 |
| CDC2L5 | 93 | 89 |
| CDK11 | 100 | 95 |
| CDK2 | 100 | 85 |
| CDK3 | 98 | 92 |
| CDK4-cyclinD1 | 85 | 47 |
| CDK4-cyclinD3 | 100 | 96 |
| CDK5 | 100 | 81 |
| CDK7 | 70 | 56 |
| CDK8 | 100 | 99 |
| CDK9 | 83 | 74 |
| CDKL1 | 68 | 61 |
| CDKL2 | 100 | 85 |
| CDKL3 | 100 | 93 |
| CDKL5 | 97 | 94 |
| CHEK1 | 100 | 85 |
| CHEK2 | 100 | 100 |
| CIT | 73 | 58 |
| CLK1 | 80 | 67 |
| CLK2 | 78 | 57 |
| CLK3 | 99 | 94 |
| CLK4 | 83 | 76 |
| CSF1R | 74 | 87 |
| CSF1R-autoinhibited | 70 | 100 |
| CSK | 100 | 91 |
| CSNK1A1 | 4.2 | 0.95 |

TABLE 1-continued

| Gene Symbol | Cmp 324 % Ctrl @ 10000 nM | Cmp A % Ctrl @ 10000 nM |
|---|---|---|
| CSNK1A1L | 81 | 1.2 |
| CSNK1D | 3.8 | 1.4 |
| CSNK1E | 1.4 | 0.1 |
| CSNK1G1 | 93 | 88 |
| CSNK1G2 | 72 | 99 |
| CSNK1G3 | 83 | 85 |
| CSNK2A1 | 56 | 53 |
| CSNK2A2 | 79 | 93 |
| CTK | 100 | 100 |
| DAPK1 | 87 | 77 |
| DAPK2 | 100 | 85 |
| DAPK3 | 100 | 86 |
| DCAMKL1 | 41 | 44 |
| DCAMKL2 | 99 | 82 |
| DCAMKL3 | 100 | 100 |
| DDR1 | 94 | 2.6 |
| DDR2 | 100 | 65 |
| DLK | 91 | 84 |
| DMPK | 100 | 100 |
| DMPK2 | 82 | 65 |
| DRAK1 | 100 | 95 |
| DRAK2 | 87 | 87 |
| DYRK1A | 87 | 74 |
| DYRK1B | 97 | 89 |
| DYRK2 | 82 | 83 |
| EGFR | 100 | 49 |
| EGFR E746-A750del | 80 | 25 |
| EGFR (G719C) | 64 | 32 |
| EGFR (G719S) | 63 | 24 |
| EGFR (L747-E749del, A750P) | 64 | 13 |
| EGFR (L747-S752del, P753S) | 57 | 11 |
| EGFR (L747-T751del, Sins) | 54 | 12 |
| EGFR (L858R) | 76 | 25 |
| EGFR (L858R, T790M) | 51 | 88 |
| EGFR (L861Q) | 64 | 29 |
| EGFR (S752-I759del) | 84 | 18 |
| EGFR (T790M) | 88 | 65 |
| EIF2AK1 | 83 | 86 |
| EPHA1 | 83 | 72 |
| EPHA2 | 98 | 70 |
| EPHA3 | 86 | 68 |
| EPHA4 | 100 | 98 |
| EPHA5 | 100 | 70 |
| EPHA6 | 100 | 96 |
| EPHA7 | 87 | 82 |
| EPHA8 | 94 | 59 |
| EPHB1 | 86 | 69 |
| EPHB2 | 99 | 82 |
| EPHB3 | 95 | 42 |
| EPHB4 | 100 | 54 |
| EPHB6 | 65 | 64 |
| ERBB2 | 99 | 49 |
| ERBB3 | 92 | 62 |
| ERBB4 | 100 | 64 |
| ERK1 | 96 | 100 |
| ERK2 | 99 | 78 |
| ERK3 | 100 | 88 |
| ERK4 | 90 | 78 |
| ERK5 | 93 | 78 |
| ERK8 | 99 | 98 |
| ERN1 | 88 | 84 |
| FAK | 99 | 92 |
| FER | 100 | 98 |
| FES | 78 | 75 |
| FGFR1 | 98 | 72 |
| FGFR2 | 63 | 53 |
| FGFR3 | 95 | 90 |
| FGFR3 (G697C) | 76 | 71 |
| FGFR4 | 100 | 100 |
| FGR | 94 | 66 |
| FLT1 | 91 | 91 |
| FLT3 | 100 | 96 |
| FLT3 (D835H) | 68 | 60 |
| FLT3 (D835Y) | 90 | 94 |
| FLT3 (ITD) | 85 | 89 |
| FLT3 (K663Q) | 100 | 99 |
| FLT3 (N841I) | 83 | 87 |
| FLT3 (R834Q) | 97 | 95 |
| FLT3-autoinhibited | 95 | 87 |
| FLT4 | 79 | 62 |
| FRK | 100 | 58 |
| FYN | 60 | 33 |
| GAK | 87 | 10 |
| GCN2 (Kin.Dom.2, S808G) | 98 | 66 |
| GRK1 | 68 | 53 |
| GRK4 | 100 | 97 |
| GRK7 | 91 | 65 |
| GSK3A | 86 | 56 |
| GSK3B | 95 | 86 |
| HASPIN | 70 | 45 |
| HCK | 100 | 65 |
| HIPK1 | 64 | 51 |
| HIPK2 | 67 | 74 |
| HIPK3 | 91 | 79 |
| HIPK4 | 100 | 83 |
| HPK1 | 86 | 82 |
| HUNK | 96 | 79 |
| ICK | 99 | 93 |
| IGF1R | 100 | 99 |
| IKK-alpha | 92 | 96 |
| IKK-beta | 99 | 90 |
| IKK-epsilon | 82 | 74 |
| INSR | 100 | 100 |
| INSRR | 100 | 100 |
| IRAK1 | 87 | 93 |
| IRAK3 | 90 | 60 |
| IRAK4 | 100 | 98 |
| ITK | 86 | 78 |
| JAK1 (JH1domain-catalytic) | 88 | 73 |
| JAK1 (JH2domain-pseudokinase) | 17 | 71 |
| JAK2 (JH1domain-catalytic) | 98 | 90 |
| JAK3 (JH1domain-catalytic) | 74 | 100 |
| JNK1 | 52 | 45 |
| JNK2 | 18 | 45 |
| JNK3 | 6 | 48 |
| KIT | 91 | 32 |
| KIT (A829P) | 79 | 86 |
| KIT (D816H) | 86 | 86 |
| KIT (D816V) | 91 | 71 |
| KIT (L576P) | 57 | 29 |
| KIT (V559D) | 69 | 19 |
| KIT (V559D, T670I) | 98 | 99 |
| KIT (V559D, V654A) | 79 | 16 |
| KIT-autoinhibited | 88 | 78 |
| LATS1 | 100 | 93 |
| LATS2 | 82 | 72 |
| LCK | 88 | 23 |
| LIMK1 | 100 | 100 |
| LIMK2 | 100 | 100 |
| LKB1 | 85 | 85 |
| LOK | 72 | 61 |
| LRRK2 | 83 | 82 |
| LRRK2 (G2019S) | 76 | 86 |
| LTK | 74 | 85 |
| LYN | 99 | 54 |
| LZK | 89 | 100 |
| MAK | 86 | 59 |
| MAP3K1 | 85 | 76 |
| MAP3K15 | 100 | 94 |
| MAP3K2 | 87 | 73 |
| MAP3K3 | 76 | 48 |
| MAP3K4 | 51 | 35 |
| MAP4K2 | 100 | 100 |
| MAP4K3 | 100 | 100 |
| MAP4K4 | 97 | 86 |
| MAP4K5 | 88 | 62 |
| MAPKAPK2 | 100 | 100 |
| MAPKAPK5 | 100 | 100 |

TABLE 1-continued

| Gene Symbol | Cmp 324 % Ctrl @ 10000 nM | Cmp A % Ctrl @ 10000 nM |
| --- | --- | --- |
| MARK1 | 100 | 99 |
| MARK2 | 91 | 85 |
| MARK3 | 100 | 88 |
| MARK4 | 100 | 100 |
| MAST1 | 86 | 75 |
| MEK1 | 97 | 39 |
| MEK2 | 82 | 24 |
| MEK3 | 80 | 60 |
| MEK4 | 70 | 43 |
| MEK5 | 66 | 51 |
| MEK6 | 98 | 73 |
| MELK | 80 | 71 |
| MERTK | 99 | 55 |
| MET | 91 | 100 |
| MET (M1250T) | 97 | 83 |
| MET (Y1235D) | 83 | 77 |
| MINK | 56 | 57 |
| MKK7 | 100 | 100 |
| MKNK1 | 96 | 100 |
| MKNK2 | 70 | 58 |
| MLCK | 94 | 53 |
| MLK1 | 100 | 95 |
| MLK2 | 100 | 91 |
| MLK3 | 83 | 83 |
| MRCKA | 99 | 94 |
| MRCKB | 100 | 100 |
| MST1 | 92 | 84 |
| MST1R | 85 | 81 |
| MST2 | 94 | 89 |
| MST3 | 98 | 71 |
| MST4 | 68 | 65 |
| MTOR | 71 | 96 |
| MUSK | 100 | 96 |
| MYLK | 86 | 71 |
| MYLK2 | 100 | 100 |
| MYLK4 | 98 | 43 |
| MYO3A | 98 | 98 |
| MYO3B | 100 | 100 |
| NDR1 | 73 | 74 |
| NDR2 | 96 | 85 |
| NEK1 | 100 | 95 |
| NEK10 | 56 | 100 |
| NEK11 | 86 | 88 |
| NEK2 | 98 | 92 |
| NEK3 | 69 | 66 |
| NEK4 | 89 | 96 |
| NEK5 | 100 | 91 |
| NEK6 | 91 | 76 |
| NEK7 | 100 | 100 |
| NEK9 | 100 | 100 |
| NIK | 100 | 100 |
| NIM1 | 96 | 87 |
| NLK | 41 | 35 |
| OSR1 | 100 | 99 |
| p38-alpha | 33 | 6 |
| p38-beta | 100 | 100 |
| p38-delta | 90 | 85 |
| p38-gamma | 61 | 79 |
| PAK1 | 75 | 71 |
| PAK2 | 92 | 79 |
| PAK3 | 95 | 75 |
| PAK4 | 98 | 89 |
| PAK6 | 100 | 86 |
| PAK7 | 96 | 96 |
| PCTK1 | 95 | 89 |
| PCTK2 | 99 | 83 |
| PCTK3 | 86 | 84 |
| PDGFRA | 86 | 89 |
| PDGFRB | 90 | 45 |
| PDPK1 | 100 | 92 |
| PFCDPK1 *P. falciparum* | 78 | 0.9 |
| PFPK5 *P. falciparum* | 100 | 100 |
| PFTAIRE2 | 100 | 100 |
| PFTK1 | 96 | 77 |
| PHKG1 | 100 | 97 |
| PHKG2 | 100 | 91 |
| PIK3C2B | 83 | 74 |
| PIK3C2G | 99 | 100 |
| PIK3CA | 100 | 89 |
| PIK3CA (C420R) | 99 | 94 |
| PIK3CA (E542K) | 98 | 90 |
| PIK3CA (E545A) | 76 | 73 |
| PIK3CA (E545K) | 82 | 77 |
| PIK3CA (H1047L) | 100 | 100 |
| PIK3CA (H1047Y) | 72 | 80 |
| PIK3CA (I800L) | 52 | 72 |
| PIK3CA (M1043I) | 100 | 100 |
| PIK3CA (Q546K) | 90 | 93 |
| PIK3CB | 100 | 100 |
| PIK3CD | 100 | 100 |
| PIK3CG | 32 | 79 |
| PIK4CB | 96 | 90 |
| PIM1 | 98 | 92 |
| PIM2 | 98 | 65 |
| PIM3 | 94 | 90 |
| PIP5K1A | 96 | 100 |
| PIP5K1C | 75 | 67 |
| PIP5K2B | 100 | 100 |
| PIP5K2C | 72 | 79 |
| PKAC-alpha | 91 | 42 |
| PKAC-beta | 95 | 63 |
| PKMYT1 | 100 | 52 |
| PKN1 | 100 | 88 |
| PKN2 | 94 | 100 |
| PKNB *M. tuberculosis* | 74 | 86 |
| PLK1 | 90 | 82 |
| PLK2 | 92 | 71 |
| PLK3 | 99 | 85 |
| PLK4 | 69 | 70 |
| PRKCD | 86 | 93 |
| PRKCE | 95 | 96 |
| PRKCH | 99 | 95 |
| PRKCI | 65 | 69 |
| PRKCQ | 100 | 88 |
| PRKD1 | 100 | 100 |
| PRKD2 | 90 | 68 |
| PRKD3 | 91 | 74 |
| PRKG1 | 100 | 100 |
| PRKG2 | 82 | 76 |
| PRKR | 96 | 90 |
| PRKX | 100 | 100 |
| PRP4 | 70 | 90 |
| PYK2 | 100 | 100 |
| QSK | 99 | 82 |
| RAF1 | 100 | 95 |
| RET | 94 | 80 |
| RET (M918T) | 88 | 56 |
| RET (V804L) | 86 | 67 |
| RET (V804M) | 100 | 100 |
| RIOK1 | 100 | 100 |
| RIOK2 | 87 | 66 |
| RIOK3 | 57 | 72 |
| RIPK1 | 100 | 99 |
| RIPK2 | 85 | 67 |
| RIPK4 | 65 | 78 |
| RIPK5 | 96 | 79 |
| ROCK1 | 96 | 100 |
| ROCK2 | 83 | 71 |
| ROS1 | 100 | 100 |
| RPS6KA4 Kin.Dom.1-N-terminal | 100 | 100 |
| RPS6KA4 Kin.Dom.2-C-terminal | 100 | 100 |
| RPS6KA5 Kin.Dom.1-N-terminal | 95 | 96 |
| RPS6KA5 Kin.Dom.2-C-terminal | 96 | 88 |
| RSK1 Kin.Dom.1-N-terminal | 86 | 72 |
| RSK1 Kin.Dom.2-C-terminal | 44 | 23 |
| RSK2 Kin.Dom.1-N-terminal | 80 | 59 |
| RSK2 Kin.Dom.2-C-terminal | 100 | 43 |
| RSK3 Kin.Dom.1-N-terminal | 100 | 83 |

TABLE 1-continued

| Gene Symbol | Target | |
| --- | --- | --- |
| | Cmp 324 % Ctrl @ 10000 nM | Cmp A % Ctrl @ 10000 nM |
| RSK3 Kin.Dom.2-C-terminal | 100 | 68 |
| RSK4 Kin.Dom.1-N-terminal | 85 | 64 |
| RSK4 Kin.Dom.2-C-terminal | 35 | 6.6 |
| S6K1 | 90 | 82 |
| SBK1 | 83 | 77 |
| SGK | 100 | 100 |
| SgK110 | 94 | 92 |
| SGK2 | 100 | 100 |
| SGK3 | 94 | 98 |
| SIK | 100 | 83 |
| SIK2 | 100 | 59 |
| SLK | 63 | 100 |
| SNARK | 98 | 91 |
| SNRK | 65 | 66 |
| SRC | 84 | 40 |
| SRMS | 100 | 93 |
| SRPK1 | 64 | 49 |
| SRPK2 | 100 | 100 |
| SRPK3 | 99 | 92 |
| STK16 | 89 | 81 |
| STK33 | 77 | 72 |
| STK35 | 100 | 100 |
| STK36 | 96 | 69 |
| STK39 | 100 | 81 |
| SYK | 100 | 86 |
| TAK1 | 81 | 56 |
| TAOK1 | 100 | 94 |
| TAOK2 | 98 | 80 |
| TAOK3 | 91 | 93 |
| TBK1 | 85 | 74 |
| TEC | 94 | 88 |
| TESK1 | 88 | 90 |
| TGFBR1 | 94 | 92 |
| TGFBR2 | 100 | 100 |
| TIE1 | 100 | 95 |
| TIE2 | 98 | 100 |
| TLK1 | 96 | 87 |
| TLK2 | 100 | 94 |
| TNIK | 78 | 53 |
| TNK1 | 97 | 99 |
| TNK2 | 100 | 81 |
| TNNI3K | 100 | 78 |
| TRKA | 77 | 86 |
| TRKB | 67 | 76 |
| TRKC | 81 | 75 |
| TRPM6 | 53 | 69 |
| TSSK1B | 100 | 100 |
| TTK | 100 | 92 |
| TXK | 93 | 45 |
| TYK2 JH1domain-catalytic | 86 | 71 |
| TYK2 JH2domain-pseudokinase | 66 | 86 |
| TYRO3 | 99 | 100 |
| ULK1 | 93 | 86 |
| ULK2 | 100 | 95 |
| ULK3 | 100 | 100 |
| VEGFR2 | 94 | 79 |
| VRK2 | 86 | 35 |
| WEE1 | 100 | 94 |
| WEE2 | 100 | 100 |
| WNK1 | 81 | 69 |
| WNK3 | 89 | 75 |
| YANK1 | 66 | 81 |
| YANK2 | 70 | 78 |
| YANK3 | 97 | 100 |
| YES | 100 | 78 |
| YSK1 | 84 | 64 |
| YSK4 | 88 | 73 |
| ZAK | 79 | 92 |
| ZAP70 | 78 | 93 |

Cmp 324 = Comparative Compound 324;
Cmp A = Compound A;

As shown in Table 1 in bold, compound A showed high binding capacity for casein kinase 1 isoforms alpha 1 (CSNK1A1), alpha 1-like (CSNK1A1L), delta (CSNK1D) and epsilon (CSNK1E); for these kinases, the binding capacities of compound A were between 2.7 and 67 fold stronger than the control compound (Comparative Compound 324).

In addition to the binding capacity, the Selectivity Score (or S-score) was calculated (Karaman, M. W. et al. A quantitative analysis of kinase inhibitor selectivity. Nat. Biotechnol. 26, 127-132 (2008). The S-score is a quantitative measure of compound selectivity. It is calculated by dividing the number of kinases that a compound binds to by the total number of distinct kinases tested, excluding mutant variants.

S-score=Number of hits/Number of assays

This value can be calculated using % Ctrl as a potency threshold—

S(35)=(number of non-mutant kinases with % Ctrl<35)/(number of non-mutant kinases tested)

S(10)=(number of non-mutant kinases with % Ctrl<10)/(number of non-mutant kinases tested)

S(1)=(number of non-mutant kinases with % Ctrl<1)/(number of non-mutant kinases tested)

and provides a quantitative method of describing compound selectivity to facilitate comparison of different compounds. The screening concentration was 10 µM. The lower the S-score, the higher the selectivity of that compound.

TABLE 2

| Compound Name | Selectivity Score Type | Number of Hits | Number of Non-Mutant Kinases | S-score |
| --- | --- | --- | --- | --- |
| Cmp 324 | S (35) | 8 | 395 | 0.02 |
| Cmp 324 | S (10) | 4 | 395 | 0.01 |
| Cmp 324 | S (1) | 0 | 395 | 0 |
| Cmp A | S (35) | 14 | 395 | 0.035 |
| Cmp A | S (10) | 8 | 395 | 0.02 |
| Cmp A | S (1) | 3 | 395 | 0.008 |

Based on the KINOMEscan's in vitro competition binding assay as of August 2007 (http://www.discoverx.com/services/drug-discovery-development-services/drug-discovery-development-services/kinase-profiling/kinomescan/scanmax), used to evaluate 38 kinase inhibitors (including 21 tyrosine kinase inhibitors, 15 serine-threonine kinase inhibitors, 1 lipid kinase inhibitor and staurosporine) against a panel of 287 distinct human protein kinases and three lipid kinases, compound A resulted having a selectivity score (Table 2) comparable to compounds approved for human use such as Lapatinimib, Imatinib and Gefitininib (data not shown).

5.2 Selectivity and IC$_{50}$ of Compound A

A two-tier strategy to determine the selectivity of compound A was applied: first, the compound was tested at a single concentration (in duplicate) to determine the %-remaining activity of the target kinase. Subsequently, the IC$_{50}$ of compound A and comparative compounds for casein kinase 1 delta were determined.

Compound A was tested against 29 kinases along with four comparative compounds: Comparative Compound 324 (S-(1,3-benzoxasol-2-yl)-4-pyridine-4-yl) pyrimidin-2-amine), Comparative Compound 987 (2-amino-3-[(4-fluorophenyl)carbonyl]indolizine-1-carboxamide), Comparative Compound 315 (4-((4-methoxyphenyl)methylene)-2-(2-thienyl)-5(4H)-oxalone; WO2010092660) and PF4800567 (3-[(3-Chlorophenoxy)methyl]-1-(tetrahydro-2H-pyran-4-yl)-1H-pyrazolo[3,4-d]pyrimidin-4-amine).

Compounds were tested in single dose duplicate mode at a concentration of 10 µM (in DMSO) and reactions were carried out at 10 µM ATP, Table 3 reports the % of remaining activity (relative to DMSO).

TABLE 3

| Kinases | Cmp A | | Cmp 324 | | Cmp 987 | | Cmp 315 | | PF4800567 | |
|---|---|---|---|---|---|---|---|---|---|---|
| ABL2/ARG | 71.29 | 70.98 | 101.22 | 96.78 | 88.07 | 83.33 | 83.42 | 89.19 | 63.54 | 68.42 |
| ALK5/TGFBR1 | 110.37 | 109.38 | 104.80 | 101.71 | 39.84 | 37.80 | 106.97 | 110.31 | 108.01 | 105.02 |
| c-Src | 61.05 | 60.86 | ND | ND | ND | ND | 104.16 | 101.24 | 49.02 | 44.05 |
| CDK5/p25 | 90.23 | 88.62 | 87.71 | 97.13 | 98.25 | 91.79 | 96.13 | 94.86 | 100.13 | 97.73 |
| CK1a1 | 5.17 | 5.37 | 65.72 | 58.48 | 20.31 | 17.57 | 33.56 | 44.41 | 28.41 | 29.28 |
| CK1e | 2.81 | 3.67 | 28.24 | 24.86 | 20.09 | 18.19 | 5.45 | 6.51 | 2.46 | 3.00 |
| CK1d | 1.15 | 0.98 | 13.29 | 11.87 | 5.71 | 5.40 | 2.23 | 1.38 | 7.70 | 8.41 |
| CK1g1 | 106.86 | 119.87 | 99.00 | 92.69 | 104.37 | 99.58 | 71.93 | 73.02 | 89.68 | 85.13 |
| CK1g2 | 95.54 | 99.83 | 57.96 | 58.69 | 77.68 | 78.23 | 47.32 | 50.52 | 89.51 | 85.95 |
| CK1g3 | 98.50 | 97.24 | 69.91 | 62.63 | 100.72 | 97.42 | 2.90 | 2.99 | 87.76 | 88.91 |
| CLK2 | 100.03 | 105.40 | 96.21 | 92.16 | 72.68 | 72.17 | 50.64 | 48.99 | 105.34 | 104.90 |
| DAPK1 | 134.25 | 124.50 | ND | ND | ND | ND | 95.96 | 90.84 | 89.99 | 92.45 |
| EGFR | 55.81 | 52.51 | 83.83 | 79.83 | 32.04 | 34.51 | 111.49 | 117.99 | 66.49 | 68.77 |
| EPHA2 | 58.98 | 55.67 | 98.65 | 105.62 | 49.40 | 50.05 | 99.04 | 96.60 | 41.16 | 39.04 |
| FGFR1 | 95.74 | 95.15 | 104.27 | 108.45 | 78.66 | 86.54 | 101.66 | 101.65 | 83.42 | 80.79 |
| GSK3b | 124.01 | 122.02 | 91.34 | 80.19 | 69.96 | 68.98 | 119.60 | 115.26 | 121.05 | 114.39 |
| JNK2 | 99.88 | 97.26 | 95.07 | 91.75 | 60.04 | 63.80 | 99.41 | 98.70 | 99.62 | 96.53 |
| KDR/VEGFR2 | 110.73 | 109.28 | 85.09 | 100.01 | 90.26 | 83.06 | 104.02 | 107.86 | 81.35 | 83.13 |
| LCK | 39.44 | 39.87 | 102.04 | 95.46 | 63.92 | 58.89 | 94.94 | 97.71 | 20.90 | 19.90 |
| MSK1/RPS6KA5 | 116.93 | 111.83 | 81.11 | 94.78 | 91.42 | 87.76 | 116.61 | 118.15 | 97.45 | 103.51 |
| P38a/MAPK14 | 35.29* | 34.47* | 53.87 | 48.46 | 17.64$ | 17.83$ | 104.71 | 107.03 | 72.97 | 71.23 |
| PDK1/PDPK1 | 106.84 | 105.50 | 104.55 | 104.88 | 95.04 | 98.31 | 104.54 | 103.28 | 102.20 | 102.92 |
| PIM3 | 124.89 | 119.96 | 99.99 | 95.35 | 88.82 | 75.10 | 60.63 | 57.54 | 107.80 | 115.55 |
| PKA | 84.30 | 82.86 | 90.80 | 90.27 | 36.94 | 33.43 | 115.73 | 112.40 | 82.77 | 83.05 |
| PKCb2 | 113.11 | 111.60 | 100.90 | 103.51 | 73.04 | 66.13 | 112.38 | 110.56 | 88.65 | 88.53 |
| RIPK2 | 93.50 | 91.39 | 92.19 | 92.78 | 36.29 | 40.46 | 93.36 | 90.19 | 48.19 | 47.57 |
| ROCK1 | 95.45 | 96.14 | 108.52 | 109.68 | 96.93 | 92.49 | 93.40 | 90.20 | 99.18 | 95.16 |
| TNIK | 94.38 | 94.12 | 74.63 | 65.72 | 68.47 | 69.49 | 101.03 | 101.11 | 90.43 | 89.69 |
| YES/YES1 | 58.43 | 60.09 | 108.04 | 95.22 | 42.84 | 40.00 | 99.02 | 99.08 | 16.42 | 15.52 |

Cmp A = Compound A;
Cmp 324 = Comparative Compound 324;
Cmp 987 = Comparative Compound 987;
Cmp 315 = Comparative Compound 315.

Compound A was found to have the highest selectivity over the comparative compounds for the casein kinases 1 alpha, delta and epsilon (in bold in Table 3), with the highest selectivity for casein kinase 1 delta and higher or comparable selectivity for casein kinases 1 alpha 1 and epsilon. In addition, compound A was found to have reduced selectivity for p38α (Table 3 indicated by *) in comparison to the other comparative compounds and in particular to Comparative Compound 987 (Table 3 indicated by $), the closest, structurally, to Compound A.

For the $IC_{50}$ calculations for casein kinase 1 delta of compound A and comparative compounds (Comparative Compound 324, Comparative Compound 987, Comparative Compound 315 and PF4800567) the compounds were tested in 10-dose with 3 fold serial dilution starting at 10 µM or 30 µM. Control compound GW5074 (Tocris®) was tested starting at 20 µM. Reactions were carried out at 10 µM ATP. Results are reported in Table 4 (for all compounds) and for Compound A the $IC_{50}$ curve is shown in FIG. 1.

TABLE 4

| | Compound | | | | | |
|---|---|---|---|---|---|---|
| | Cmp A | Cmp 324 | Cmp 987 | Cmp 315 | PF4800567 | GW5074 |
| $IC_{50}$ (M): | 1.74E−08 | 4.83E−07 | 3.10E−07 | 4.35E−07 | 3.55E−07 | 1.13E−07 |

Cmp A = Compound A;
Cmp 324 = Comparative Compound 324;
Cmp 987 = Comparative Compound 987;
Cmp 315 = Comparative Compound 315.

Compound A showed higher potency with respect to the positive control compound GW5074 and Comparative Compounds 324, 987 and 315 (Table 4). In particular, the $IC_{50}$ for Compound A was 17-fold more potent that Comparative Compound 987.

5.3 Cytotoxicity Screening Panel

The cytotoxicity screening panel was performed by Cyprotex® according to their established protocols. HepG2 cells were plated on 96-well tissue culture treated black walled clear bottomed polystyrene plates, 100 µL per well. The cells were dosed with compound A and comparative compound 324 (WO2012080727; 5-(1,3-benzoxazol-2-yl)-4-(pyridine-4-yl)pyrimidin-2-amine) amine) at 0.04 µm, 0.1

μM, 0.4 μM, 1.0 μM, 4.0 μM, 10 μM, 40 μM and 100 μM. At the end of the incubation period (72 h), the cells were loaded with the relevant dye/antibody for each cell health marker. The plates were then scanned using an automated fluorescent cellular imager, ArrayScan® VTI (Thermo Scientific Cellomics).

Cytotoxicity was assessed using a multiparametric approach using High Content Screening (HCS) O'Brien P and Haskins J R (2007) High Content Screening: A Powerful Approach to Systems Cell Biology and Drug Discovery Ed. Taylor et al.; 415-425). Decreased cell count is a direct indication of toxicity, but many compounds cause sub-lethal toxicities that do not cause changes in cell viability over the incubation period. This assay scores compounds across direct and indirect measure of toxicity.

TABLE 5

| Cell Health Parameter | MEC (μM) | $AC_{50}$ (μM) | First Signal MEC | $AC_{50}$ |
|---|---|---|---|---|
| Cell Count | 2.75↓ (NR) | 7.88↓ (NR) | x | |
| Nuclear size | 2.44↑ (NR) | 12.3↑ (NR) | | |
| DNA structure | 15.1↑ (7.33↑) | >100↑# (>100↑#) | | |
| Cell membrane permeability | 1.26↑ (11.1↑) | >40↑# (>100↑#) | X (X) | |
| Mitochondrial membrane potential | 3.31↓ (17.2↑) | 43.4↓ (>100↑#) | | |
| Mitochondrial mass | 1.34↑ (16.8↓) | >40↑# (>100↓#) | | |
| Cytochrome c | NR (22.2↑) | NR (82.0↑) | | (X) |

MEC indicates the minimum effective concentration that significantly crosses vehicle control threshold; $AC_{50}$ indicates the concentration at which 50% maximum effect is observed for each health parameter.
NR indicates no response observed.
↓↑indicates the direction of response.
indicates that the $AC_{50}$ was greater than the maximum surviving concentration.
Values for comparative compound 324 are indicated in brackets.

Both compound A and comparative compound 324 decrease the number of cells per well at a concentration well above the $IC_{50}$. Decreased cell count indicates toxicity due to necrosis, apoptosis or a reduction in cellular proliferation.

An increase in nuclear size can indicate necrosis or G2 cell cycle arrest, whilst an increase in DNA structure can indicate chromosomal instability and DNA fragmentation. Both compound A and comparative compound 324 increase nuclear size and DNA structure at concentrations well above their $IC_{50}$.

Similarly, compound A and the comparative compound 324 both increased cell membrane permeability (a general indicator of cell death) at concentrations well above their $IC_{50}$.

Increase in mitochondrial mass and mitochondrial membrane potential (Δψm) implies mitochondrial swelling or an adaptive response to cellular energy demands, whilst a decrease in mitochondrial membrane potential indicates mitochondrial toxicity, as well as a potential role in apoptosis signaling.

Finally, an increase in cytochrome c release is one of the hallmarks of the apoptosis signalling cascade. No response was observed for Compound A vis-a-vis the comparative compound 324.

5.4 Pharmacokinetics of Compounds A in Male CD-1 Mice

Six groups of male CD-1 mice of approximately 25-35 g (about 8 weeks of age) were dosed with Comparative compound 324 and Compound A intravenously (IV) (in 10% DMSO:90% Hydroxypropyl-β-cyclodextrin (20% aq. w/v)) or orally (PO) (in 0.5% w/v methylcelluose (aq.) according to the regimen shown in Table 6.

TABLE 6

| Group | Compound | Dose Route | Dose level (mg/kg) |
|---|---|---|---|
| 1 (n = 24) | Comparative Compound | IV | 3 |
| 2 (n = 21) | Compound | PO | 3 |
| 3 (n = 21) | 324 | PO | 30 |
| 4 (n = 24) | Compound A | IV | 3 |
| 5 (n = 21) | | PO | 3 |
| 6 (n = 21) | | PO | 30 | n = number of mice per group.

Intravenous doses was administered into a tail vein at a constant dose volume of 5 mL/kg to achieve a dose level of 3 mg/kg. Oral doses were administered as a single bolus dose via syringe with attached polypropylene gavage tube at a constant dose volume of 10 mL/kg to achieve dose levels of 3 mg/kg (groups 2 and 4) and 30 mg/kg (group 3 and 6).

Following dosing, blood samples were collected into individual $K_3$EDTA tubes by cardiac puncture under terminal anaesthesia (isoflurane) from 3 animals per timepoint. Following collection animal were sacrificed by cervical dislocation. Samples were taken at 5, 15 and 30 minutes and then 1, 2, 4, 8 and 24 hours post-IV dose and 15 and 30 minutes and then 1, 2, 4, 8 and 24 hours post-OP dose.

Upon collection, blood samples were centrifuged at 10,000×g, 2 minutes at 4° C. and the resultant plasma was drawn off and stored at −20° C. for analysis by LC-MS/MS of the concentration of the compounds. The remaining blood call pellet was discarded.

Pharmacokinetic parameters were derived by non-compartmental analysis (linear/logarithmic trapezoidal) using WinNonlin (Version 4.1 or higher) software. The following parameters were determined from the plasma concentration-time profile:

Cmax (ng/mL): Maximum measured concentration

Tmax (h): Time at which maximum concentration was apparent

T1/2 (h): Terminal half-life $AUC_{C-t}$ (h*ng/mL: Area under the curve from 0 to last quantifiable data point $AUC_{c-28}$ (h*ng/mL): Area under the curve from 0 to 24 hours $AUC_{t-inf}$ (h*ng/mL): Area under curve from time 0 to infinity (predicted)

AUG extrapolated (AUCex): Percent of $AUC_{C-inf}$ that is extrapolated (predicted)

CL/F* (mL/min/kg): Volume of plasma cleared of drug per unit time (predicted)

Vdss/F* (mL/min/kg) (Vz/F): Volume of distribution, at steady state (predicted)

F %: Oral bioavailability

Pharmacokinetics are shown in Table 7. Compound A was completely cleared after 24 hours of administration.

TABLE 7

| Name (G) | Dose | Cmax | Tmax | T1/2 | $AUC_{0-t}$ | $AUC_{0-24h}$ | $AUC_{0-inf}$ | AUCex | Cl | Vz |
|---|---|---|---|---|---|---|---|---|---|---|
| Intravenous administration ||||||||||||
| Cmp 324 (1) | 3 | 1150 | 0.083 | 0.091 | 304 | 315 | 309 | 1.9 | 162 | 1270 |
| Cmp A (4) | 3 | 1680 | 0.083 | 0.23 | 498 | 502 | 499 | 0.1 | 100 | 2000 |

| Name (G) | Dose | Cmax | Tmax | T1/2 | $AUC_{0-t}$ | $AUC_{0-24h}$ | $AUC_{0-inf}$ | AUCex | Cl/F | Vz/F | F |
|---|---|---|---|---|---|---|---|---|---|---|---|
| Oral administration |||||||||||||
| Cmp 324 (2) | 3 | 14 | 0.25 | NC | 8.66 | 11.1 | NC | NC | NC | NC | 3 |
| Cmp 324 (3) | 30 | 666 | 0.5 | NR | 1210 | 1590 | NR | NR | NR | NR | 40 |
| Cmp A (5) | 3 | 47 | 0.25 | 0.49 | 32.4 | 35.4 | 34.6 | 6.3 | 1450 | 61400 | 7 |
| Cmp A (6)* | 30 | 237 | 0.5 | 3.5 | 470 | 659 | 576 | 18.5 | 868 | 264000 | 9 |

G = Group;
Cmp A = Compound A;
Cmp 324 = Comparative Compound 324;
NC = not determined;
NR = not reported as falls exclusion criteria;
*one PK outlier excluded.

5.5 In-Vivo Efficacy Assay with Tau Transgenic Mice

TMHT (Thy-1 Mutated Human Tau) mouse (developed by QPS® Austria, http://www.qps-austria.com) represent a suitable model not only for Alzheimer's Disease but also for other Tauopathies such as Frontotemporal Dementia and Parkinsonism linked to chromosome 17 (FTDP-17) and Niemann Pick's disease. Various compounds of different classes (among them also antibody treatments) were positively tested for their efficacy in the TMHT model. Published examples are the γ-secretase modulator CHF5074 (Lanzilotta A, et al. The γ-secretase modulator CHF5074 reduces the accumulation of native hyperphosphoxylated tau in a transgenic mouse model of Alzheimer's disease. J Mol Neurosci. 45(1):22--33 (2010)), sodium selenate (Corcoran N M et al. Sodium selenate specifically activates PP2A phosphatase, dephosphorylates tau and reverses memory deficits in an Alzheimer's disease model. J Clin Neurosci. 17(8):1025-33 (2010)) and grape-seed polyphenol extract (Wang J et al. Grape derived polyphenols attenuate tau neuropathology in a mouse model of Alzheimer's disease. J Alzheimers Dis. 22(2):653-61 (2010)).

Starting at 8.5 months (±2 weeks) of age, TMHT mice received compound A, comparative compound 324 or comparative compound PF4800567 (3-[(3-Chlorophenoxy)methyl]-1-(tetrahydro-2H-pyran-4-yl)-1H-pyrazolo[3,4-d]pyrimidin-4-amine) or vehicle (0.5% w/v methylcellulose) for 8 weeks (54 applications) at a dosage of 30 mg/kg body weight, orally via gavage. The effects of the compounds on learning in the Morris Mater Maze (MWM) were evaluated. Blood (plasma) and brain samples were collected after sacrification. Samples collected at sacrifice were plasma, left cortex, left hippocampus, right cortex, right hippocampus, remainder of left brain hemisphere, remainder of right brain hemisphere.

In total 48 animals were used and allocated to 4 treatment groups. Table 8 describes the animals, cohort and treatment group allocation, sex and age of the animals.

TABLE 8

| Cohort | Group | Treatment | Sex | Start Age [months] |
|---|---|---|---|---|
| I | A | Vehicle | m | 8.75 |
| I | A | Vehicle | f | 8.75 |
| I | A | Vehicle | f | 8.75 |
| I | A | Vehicle | f | 8.75 |
| I | A | Vehicle | m | 8.42 |
| I | A | Vehicle | m | 8.42 |
| I | B | Cmp A | m | 8.75 |
| I | B | Cmp A | m | 8.75 |
| I | B | Cmp A | f | 8.45 |
| I | B | Cmp A | f | 8.45 |
| I | B | Cmp A | f | 8.45 |
| I | B | Cmp A | m | 8.32 |
| I | C | Cmp 324 | f | 8.75 |
| I | C | Cmp 324 | f | 8.75 |
| I | C | Cmp 324 | m | 8.75 |
| I | C | Cmp 324 | m | 8.75 |
| I | C | Cmp 324 | f | 8.75 |
| I | C | Cmp 324 | m | 8.45 |
| I | D | PF4800567 | m | 8.75 |
| I | D | PF4800567 | f | 8.75 |
| I | D | PF4800567 | f | 8.75 |
| I | D | PF4800567 | f | 8.45 |
| *I | D | PF4800567 | m | 8.42 |
| I | D | PF4800567 | m | 8.32 |
| II | A | Vehicle | f | 8.65 |
| II | A | Vehicle | f | 8.65 |
| II | A | Vehicle | m | 8.55 |
| II | A | Vehicle | f | 8.52 |
| II | A | Vehicle | f | 8.35 |
| II | A | Vehicle | m | 8.19 |
| II | B | Cmp A | f | 8.55 |
| II | B | Cmp A | f | 8.55 |
| II | B | Cmp A | f | 8.52 |
| II | B | Cmp A | m | 8.19 |
| II | B | Cmp A | m | 8.19 |
| II | B | Cmp A | f | 8.35 |
| II | C | Cmp 324 | m | 8.02 |
| II | C | Cmp 324 | m | 8.02 |
| II | C | Cmp 324 | f | 8.65 |
| II | C | Cmp 324 | f | 8.65 |

TABLE 8-continued

| Cohort | Group | Treatment | Sex | Start Age [months] |
|---|---|---|---|---|
| II | C | Cmp 324 | f | 8.35 |
| II | C | Cmp 324 | f | 8.52 |
| II | D | PF4800567 | f | 8.35 |
| II | D | PF4800567 | f | 8.55 |
| II | D | PF4800567 | f | 8.55 |
| II | D | PF4800567 | m | 8.35 |
| II | D | PF4800567 | m | 8.35 |
| II | D | PF4800567 | f | 8.19 |

Cmp 324 = control;
Cmp A = Compound A;
f = female; m = male

Of the 48 transgenic animals, one (indicated by * in Table 8) was euthanized 4 days after treatment start due to humane end point regulations (paralysis and high grade of dehydration). The death rate was within a normal range of untreated transgenic animals in this age and observation period.

The start position of the mouse and the position of the platform (FIG. 1) in the different trials of the MWM were as indicated in Table 9:

TABLE 9

| Day | Trial 1 | Trial 2 | Trial 3 | Probe Trial | Platform |
|---|---|---|---|---|---|
| 1 | SE | NW | SW | — | NE |
| 2 | SE | NW | SW | — | NE |
| 3 | SE | NW | SW | — | NE |
| 4 | SE | NW | SW | SW | NE |

Figure 2:
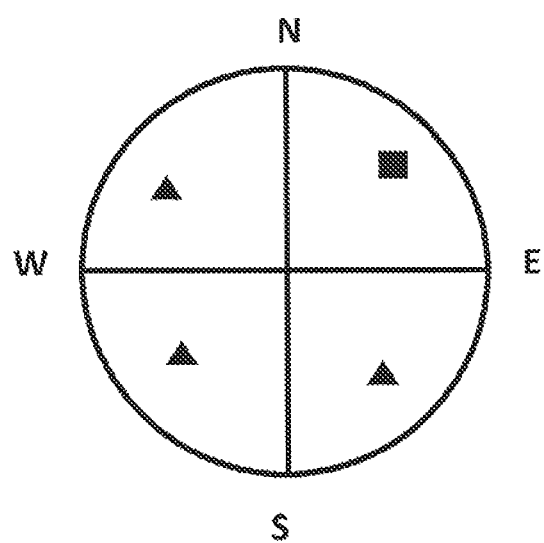
FIG. 2. Depiction of the Morris Water Maze. The black triangles indicate the start positions of the mice and the black square indicates the target platform. N=North; W=West; S=South and E=East.

SE = South East; NW = North West; SW = South West; NE = North East with reference to FIG. 2.

The effect on cognition in the Morris Water Maze was evaluated by the analysis of:
path length (length of the trajectory [meter] to reach the target)
escape latency (time [seconds] to reach the target)
deltas in path length and escape latencies between day 1 on all following days
abidance in the target quadrant in probe trial A descriptive statistical analysis was performed on all evaluated parameters. All data were represented as mean ±standard error of mean (SEM). MWM learning curve data of three trials per day were averaged.

Figure 3:
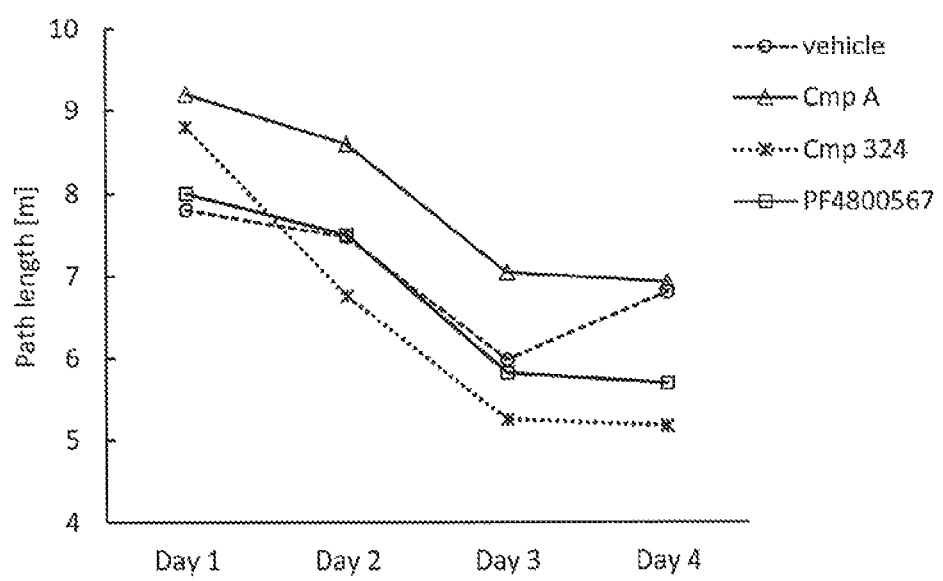
FIG. 3. Path length (length of the trajectory [meter] to reach the target) in the Morris Water Maze of animals of groups A to D. Graphs represent mean for each day (average of the 3 trials par day) over 4days.
Figure 4:
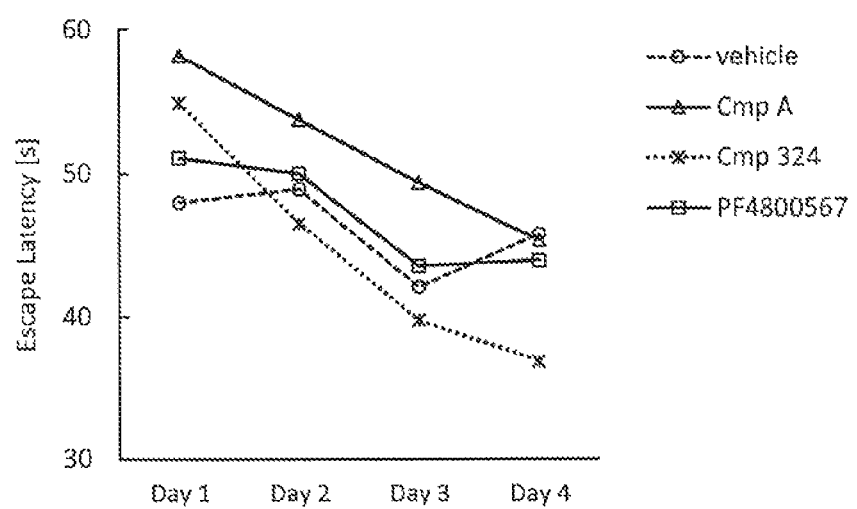
FIG. 4. Escape latency (time [seconds] to reach the target) in the Morris Water Masse of animals of groups A to D, Graphs represent mean far each day (average of the 3 trials per day) over 4 days.

Results in the MWM, revealing cognitive functions are shown in FIGS. 3 and 4. Over a period of 4 days, the ability to find a hidden platform using visual cues was measured performing 3 trials a day. By comparison of the learning curves, the cognitive abilities of the different treatment groups and possible drug effects were evaluated.

FIG. 3 shows the means for each day over 4 days; Table 10 shows the values of the means and the standard error of the means (SEMs) for each compound over the 4 days testing. Non-performers were excluded.

TABLE 10

| | Mean ± SEM | | | |
|---|---|---|---|---|
| | Day 1 | Day 2 | Day 3 | Day 4 |
| Vehicle | 7.81 ± 0.64 | 7.48 ± 0.65 | 5.99 ± 0.61 | 6.82 ± 0.69 |
| Cmp A | 9.20 ± 0.46 | 8.60 ± 0.52 | 7.05 ± 0.62 | 6.94 ± 0.62 |
| Cmp 324 | 8.81 ± 0.55 | 6.77 ± 0.64 | 5.25 ± 0.58 | 5.17 ± 0.62 |
| PF4800567 | 8.00 ± 0.54 | 7.51 ± 0.56 | 5.83 ± 0.61 | 5.70 ± 0.58 |

Cmp A = Compound A; Cmp 324 = Comparative Compound 324; SEM = standard of error of the mean.

Learning curves for path length to reach the target showed statistically significant learning (Table 11) when defined as a shortening of the path length compared to day 1 with respect to the negative control (vehicle) (in bold in Table 11).

TABLE 11

| Group | Day 1 to Day 2 | Day 1 to Day 3 | Day 1 to Day 4 |
|---|---|---|---|
| A. Vehicle | $P > 0.05$ | $P < 0.05$ | $P > 0.05$ |
| B. Cmp A | $P > 0.05$ | $P < 0.01$ | $P < 0.01$ |
| C. Cmp 324 | $P < 0.05$ | $P < 0.001$ | $P < 0.001$ |
| D. PF4800567 | $P > 0.05$ | $P < 0.01$ | $P < 0.01$ |

Cmp A = compound A;
Cmp 324 = comparative compound 324

In terms of escape latency, i.e. time to reach the target, a similar result was observed as for the path length. FIG. 4 shows the means for each day over 4 days; Table 12 shows the values of the means and the standard error of the means (SEMs) for each compound over the 4 days testing. Non-performers were excluded.

TABLE 12

| | Mean ± SEM | | | |
|---|---|---|---|---|
| | Day 1 | Day 2 | Day 3 | Day 4 |
| Vehicle | 48.0 ± 3.34 | 49.0 ± 3.59 | 42.1 ± 3.58 | 45.9 ± 3.98 |
| Cmp A | 58.1 ± 1.44 | 53.7 ± 2.41 | 49.4 ± 3.23 | 45.4 ± 3.22 |
| Cmp 324 | 54.9 ± 2.66 | 46.6 ± 3.82 | 39.8 ± 3.95 | 36.9 ± 3.87 |
| PF4800567 | 51.1 ± 3.10 | 50.0 ± 3.49 | 43.6 ± 3.86 | 44.0 ± 3.72 |

Cmp A = Compound A; Cmp 324 = Comparative Compound 324; SEM = standard of error of the mean.

Again, comparative compound 324 treated animals showed the steepest learning curve of all groups followed by the Compound A treated animals (FIG. 4, Table 13 in bold). For the escape latency, learning did not reach statistical significance for vehicle and PF4800567 treated animals.

TABLE 13

| Group | Day 1 to Day 2 | Day 1 to Day 3 | Day 1 to Day 4 |
|---|---|---|---|
| A. Vehicle | $P > 0.05$ | $P > 0.05$ | $P > 0.05$ |
| B. Cmp A | $P > 0.05$ | $P > 0.05$ | $P < 0.05$ |
| C. Cmp 324 | $P > 0.05$ | $P < 0.01$ | $P < 0.001$ |
| D. PF4800567 | $P > 0.05$ | $P > 0.05$ | $P > 0.05$ |

Cmp A = compound A;
Cmp 324 = comparative compound 324

The swim speed of the animals decreased slightly from day 1 to 4 that is typically seen in the MWM but it was not statistically significant. Similarly, in the probe trial performed at the end of the MWM, the abidance in the target quadrant with the removed platform was evaluated. No significant difference between the treatment groups ware observed. This result is often seen in the behaviour of mice even with potent compounds.

5.6 Determination of Compound A in the Plasma and Brains of CD-1 Mice.

Plasma and brain samples derived from the experiments in 5.5 were pooled from single time point and were analysed for the presence and concentration of Comparative Compound 324 and Compound A by LC-MS/MS after protein precipitation over the calibration range of 0.5-10,000 ng/mL. Chrysin (Sigma®), control mouse plasma and brain (obtained from a commercial supplier) were used as internal standards.

All instrument control, data collection, peak area integration and storage were performed using Thermo Finnigan TSQ Quantum Ultra Mass Spectrometer in conjunction with LCQuan software (v.2.5.6). The mass spectrometer response (peak area ratio of analyte to internal standard) of each calibration standard was calculated by Watson LIMS (v. 7.2) and plotted against the nominal concentration. A weighted least square quadratic regression analysis was used to calculate an equation of the calibration line using one of the standard fits in Watson LIMS. Concentration of Comparative Compound 324 and Compound A in the plasma and brain samples were back calculated from the calibration lines to 3 significant figures. All results reported are from samples that passed the following criteria:

$$\text{RE (relative error)}(\%) = \frac{\left(\begin{array}{c}\text{mean calculated concentration}-\\ \text{nominal concentration}\end{array}\right)}{\text{nominal concentration}} \times 100$$

At least 7 calibration standards within ±20% RE of their target concentrations.

At least 66% of QC samples within ±20% RE of their respective target values. Within at least one acceptable at each level when n=3 and two when n=6.

The analytical method was as summarised below in Table 14:

TABLE 14

| HPLC conditions | |
|---|---|
| Autosampler | CTC HTS PAL |
| Typical injection volume | 10 μL |
| Wash 1 | Methanol |
| Wash 2 | Acetonitrile |
| HPLC system | Agilent 1200 system |
| Flow rate | 1.0 mL/min |
| Analytical column | Phenomenex Kinetix XB-C18 2.6 μm 50 × 2.1 mm |
| Column temperature | 40° C. |
| Run Time | 2.5 minutes |
| Mobile phase A | 10 mM Ammonium Bicarbonate pH 9 (aq) |
| Mobile phase B | Acetonitrile |

| Time (min) | % A | % B |
|---|---|---|
| initial | 95 | 5 |
| 0.1 | 95 | 5 |
| 1.0 | 5 | 95 |
| 2.0 | 5 | 95 |
| 2.01 | 95 | 5 |
| 2.5 | 95 | 5 |

TABLE 14-continued

| MS/MS conditions (Thermo TSQ Quantum Ultra) | |
|---|---|
| Ionisation interface | HESI |
| Vapouriser Temperature (° C.) | 350 |
| Sheath Gas Pressure (psi) | 50 |
| Aux Gas Pressure (psi) | 40 |
| Capillary Temp (° C.) | 270 |
| Ionspray Voltage (v) | 3750 |

| Compound | Precursor ion (m/z) | Product ion (m/z) | Dwell time (msec) | Polarity | Typical R.T. (mins) |
|---|---|---|---|---|---|
| Cmp 324 | 290.1 | 183.9 | 50 | positive | 0.92 |
| Cmp A | 312.3 | 295.1 | 50 | positive | 0.96 |
| Chrysin | 255.1 | 152.9 | 50 | positive | 0.93 |

Mass for precursor/product ions are nominal.
Cmp 324 = Comparative Compound 324; Cmp A = Compound A.

In total 32 samples were analysed. Quality control (QC) samples at concentration of 10, 100 and 1000 ng/mL were freshly prepared on the day of the analysis. Tables 15 and 16 show the concentration (in ng/mL) of Comparative Compound 324 and Compound A, respectively, in plasma and in the cortex, hippocampus and rest of the brain of TMHT mice of experiment 5.5.

TABLE 15

| | Mouse single identifier | | | | | | | |
|---|---|---|---|---|---|---|---|---|
| Sample | 183a | 185a | 190 | 191 | 193 | 194 | 203 | 211 |
| Plasma | 295 | 1450 | 34.2 | 230 | 225 | 10.5 | 287 | 138 |
| Cortex | 14.3 | 108 | 1.98 | 10.5 | 10.7 | 0.536 | 15.3 | 6.41 |
| Hippocampus | 11.9 | 87.0 | BLQ | 12.6 | 11.5 | BLQ | 15.1 | 6.12 |
| Rest of brain | 16.2 | 122 | 9.97 | 9.75 | 10.8 | 1.12 | 16.0 | 7.09 |

BLQ = below the limit of quantification;

TABLE 16

| | Mouse single identifier | | | | | | | |
|---|---|---|---|---|---|---|---|---|
| Sample | 154a | 156a | 179 | 181 | 183 | 187a | 207 | 218 |
| Plasma | 12.6 | 207 | 203 | 274 | 188 | 16.9 | 319 | 25.6 |
| Cortex | BLQ | 12.6 | 9.67 | 14.9 | 8.92 | 2.51 | 17.7 | BLQ |
| Hippocampus | BLQ | 10.5 | 8.23 | 12.8 | 9.33 | BLQ | 10.3 | BLQ |
| Rest of brain | BLQ | 12.7 | 10.5 | 14.1 | 12.9 | BLQ | 19.0 | 2.66 |

BLQ = below the limit of quantification;

These results show that compound A was found at a consistent concentration in the brain at about 11.13 ng/mL±1.05 (Mean ±SEM) and was distributed in all the analysed areas of the brain.

5.7 Physicochemical Parameters of Compound A.

Physicochemical parameters were calculated via the software ChemAxon's JChem for Office suite (v. 15.4.2700, 2610). Results are shown in table 17 below.

TABLE 17

| | 119 CNS drug average | | | Comparative Compounds | | |
|---|---|---|---|---|---|---|
| | Most desirable | Least desirable | Cmp A | Cmp 987 | PF-670462 | PF-4800567 |
| logP | ≤3 | >5 | 2.11 | 2.45 | 3.93 | 1.84 |
| pKa | ≤8 | >10 | N/A | N/A | 4.78 | 6.29 |
| logD | ≤2 | >4 | 2.11 | 2.45 | 3.9 | 1.8 |
| MW | ≤360 | >500 | 311.3 | 297.3 | 337.4 | 359.8 |
| TPSA (Å2) | >40, ≤90 | ≤20, >120 | 76.6 | 90.6 | 69.6 | 88.1 |
| Lipinski HBD | ≤0.5 | >3.5 | 3 | 4 | 2 | 2 |

TPSA = Topological Polar Surface Area;
Lipinski HBD (Lipinski CA et al.
Experimental and computational approaches to estimate solubility and permeability in drug discovery and development settings, Adv. Drug Deliv. Rev. 46 (1-3): 3-26 (2001).

Compound A has improved physicochemical parameters compared to Comparative Compound 987, PF670462 and PF4800567 (both Tocris®). In addition, Compound A's physicochemical parameters were within the most desirable ranges typical of 119 marketed drugs for the central nervous system (Wager T. T, et al., ACS Chem. Neurosci. (2010), 1, 435-449). In particular, Compound A showed improved blood-brain barrier (BBB) permeation when compared to its structurally closest compound, comparative compound 987 with a TPSA of 76.6 Å$^2$, well within the most desirable range.

The invention claimed is:

1. A compound having the structure

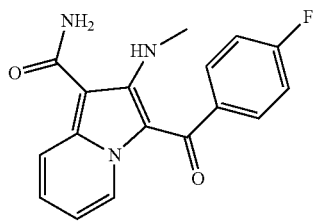 [SMILES: CNc1c(C(N)=O)c2ccccn2c1C(=O)c1ccc(F)cc1]

or a pharmaceutically acceptable salt thereof.

2. A pharmaceutical composition comprising the compound or the pharmaceutically acceptable salt thereof as defined in claim 1, and one or more pharmaceutically acceptable carriers or excipients.

3. A combination comprising the compound or the pharmaceutically acceptable salt thereof as defined in claim 1, and an anti-amyloid agent, wherein the anti-amyloid agent comprises a BACE inhibitor, a gamma-secretase inhibitor, an anti-amyloid-beta antibody, or an amyloid beta aggregation inhibitor.

4. A method of inhibiting casein kinase 1 delta activity in a subject in need thereof, wherein the method comprises administering to the subject a therapeutically effective amount of the compound or the pharmaceutically acceptable salt thereof as defined in claim 1.

5. A method of treating Alzheimer's disease, comprising administering to a subject in need thereof a therapeutically effective amount of the compound or the pharmaceutically acceptable salt thereof as defined in claim 1.

6. The method of claim 4, wherein the compound or the pharmaceutical acceptable salt thereof is administered as a pharmaceutical composition comprising a tablet, capsule, powder or liquid.

7. The method of claim 4, wherein the compound or the pharmaceutical acceptable salt thereof is administered as a pharmaceutical composition formulated for oral administration.

8. The method of claim 4, wherein the compound or the pharmaceutical acceptable salt thereof is administered as a pharmaceutical composition formulated for intravenous, cutaneous or subcutaneous, nasal, intramuscular, or intraperitoneal administration.

9. The method of claim 4, wherein the compound or the pharmaceutical acceptable salt thereof is administered as a pharmaceutical composition formulated as a liquid.

10. The method of claim 4, wherein the compound or the pharmaceutical acceptable salt thereof is administered as a pharmaceutical composition further comprising at least one pharmaceutically acceptable excipient, carrier, buffer, or stabilizer.

11. The method of claim 4, wherein the compound or the pharmaceutical acceptable salt thereof is administered as a pharmaceutical composition formulated as a parenterally-acceptable aqueous solution.

12. The method of claim 5, wherein the compound or the pharmaceutical acceptable salt thereof is administered as a pharmaceutical composition comprising a tablet, capsule, powder or liquid.

13. The method of claim 5, wherein the compound or the pharmaceutical acceptable salt thereof is administered as a pharmaceutical composition formulated for oral administration.

14. The method of claim 5, wherein the compound or the pharmaceutical acceptable salt thereof is administered as a pharmaceutical composition formulated for intravenous, cutaneous or subcutaneous, nasal, intramuscular, or intraperitoneal administration.

15. The method of claim 5, wherein the compound or the pharmaceutical acceptable salt thereof is administered as a pharmaceutical composition formulated as a liquid.

16. The method of claim 5, wherein the compound or the pharmaceutical acceptable salt thereof is administered as a pharmaceutical composition further comprising at least one pharmaceutically acceptable excipient, carrier, buffer, or stabilizer.

17. The method of claim 5, wherein the compound or the pharmaceutical acceptable salt thereof is administered as a pharmaceutical composition formulated as a parenterally-acceptable aqueous solution.

* * * * *